United States Patent [19]

Hamano et al.

[11] 4,421,763

[45] Dec. 20, 1983

[54] CYCLOHEXANE DERIVATIVES, PROCESS FOR PREPARATION THEREOF AND MEDICINES CONTAINING THESE CYCLOHEXANE DERIVATIVES

[75] Inventors: Sachiyuki Hamano; Shinichi Kitamura, both of Tokyo; Toshiji Igarashi, Tokorozawa; Yoshikage Nakajima, Tokyo, all of Japan

[73] Assignee: Eisai Co., Ltd., Tokyo, Japan

[21] Appl. No.: 362,358

[22] Filed: Mar. 26, 1982

Related U.S. Application Data

[62] Division of Ser. No. 133,694, Mar. 25, 1980, Pat. No. 4,350,705.

[30] Foreign Application Priority Data

Mar. 31, 1979 [JP] Japan .................................. 54-37696
Sep. 10, 1979 [JP] Japan ................................ 54-115240

[51] Int. Cl.³ .................... A61K 31/34; A61K 31/12; A61K 31/165; C07C 49/30; C07D 307/34

[52] U.S. Cl. ............................... 424/285; 260/465 D; 260/465 E; 260/465 F; 260/465 G; 260/465 H; 424/304; 424/311; 424/324; 424/330; 424/331; 549/498; 560/138; 560/140; 560/141; 564/169; 564/307; 568/306; 568/329

[58] Field of Search .................. 560/138, 140, 141; 568/329, 306; 564/169, 307; 549/498; 424/285, 304, 311, 324, 330, 331; 260/465 D, 465 E, 465 F, 465 G, 465 H

[56] References Cited

FOREIGN PATENT DOCUMENTS 48-32850 5/1973 Japan .
49-30343 3/1974 Japan .
558318 1/1975 Switzerland .

*Primary Examiner*—Natalie Trousof
*Assistant Examiner*—Patricia M. Scott
*Attorney, Agent, or Firm*—Flynn, Thiel, Boutell & Tanis

[57] ABSTRACT

Derivatives of 2-substituted-cyclohexane-1,3-diones possessing antihypertensive activity.

11 Claims, No Drawings

CYCLOHEXANE DERIVATIVES, PROCESS FOR PREPARATION THEREOF AND MEDICINES CONTAINING THESE CYCLOHEXANE DERIVATIVES

This is a division, of application Ser. No. 133 694, filed Mar. 25, 1980 now U.S. Pat. No. 4,350,705.

The present invention relates to cyclohexane derivatives having excellent medicinal activity, processes for the preparation thereof and medicines containing these cyclohexane derivatives.

More specifically, the present invention relates to cyclohexane derivatives represented by the following general formula [I], processes for the preparation thereof and medicines containing same.

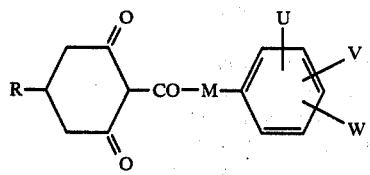

in which R is hydrogen, phenyl, substituted phenyl or furyl; M is $+CH_2+_m$, wherein m is zero or an integer of one to four, or —NH—; and U, V and W are (1) X, Y and Z, respectively, which can be the same or different and are hydrogen, a lower alkyl, a lower alkoxy, a lower alkyl-carbonyloxy group, hydroxy, a lower alkylsulfonyl, nitro, cyano or a halogen, or (2) U and V are located at 3- and 4-positions, respectively, and form —O—A—O— in which A is $+CH_2+_n$, wherein n is the integer one or two, $>CR_1R_2$, wherein $R_1$ and $R_2$, which can be the same or different, are a lower alkyl or phenyl, or $>C=O$, and W is hydrogen; with the provisos that R is not hydrogen when M is $+CH_2+$ or —NH— and U, V and W are X, Y and Z; and that M is $+CH_2+_m$ when U and V form —O—A—O—.

The compound as defined in the formula [I] can be classified into two groups as defined in formulae [II] and [III], respectively.

One group of compounds within the scope of formula [I] is shown by the following formula [II]

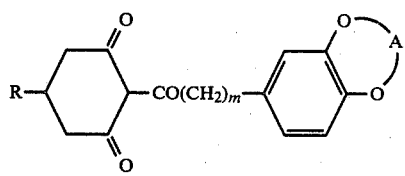

wherein R stands for a hydrogen atom, an unsubstituted or substituted phenyl group or a furyl group, m is an integer of from 0 to 4, and A stands for a group represented by the formula —$(CH_2)_{\overline{n}}$ in which n is an integer of 1 or 2, or a group represented by the formula

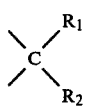

in which $R_1$ and $R_2$, which can be the same or different, stand for a lower alkyl group or a phenyl group, or a group represented by the formula $>C=O$.

In the above general formula [II], R stands for a hydrogen atom, an unsubstituted or substituted phenyl group or a furyl group. As the substituent on the substituted phenyl group, there can be mentioned, for example, linear and branched lower alkyl groups having 1 to 6 carbon atoms, such as methyl, ethyl, n-propyl, isopropyl, n-pentyl, 1-ethylpropyl, isoamyl and n-hexyl groups, lower alkoxy groups having 1 to 6 carbon atoms, such as methoxy, ethoxy, n-propxy, isopropoxy, n-butoxy and isobutoxy groups, a hydroxyl group, halogen atoms such as chlorine, bromine, fluorine and iodine, halogenated alkyl groups such as a trifluoromethyl group, an amino group, substituted amino groups such as N,N-dimethylamino and N,N-diethylamino groups, and groups of the formula —O—$(CH_2)_a$—O— in which a is an integer of 1 or 2, which is bonded to any two adjacent carbon atoms of the phenyl nucleus, such as methylenedioxy and ethylenedioxy groups. The number of the substituents is 1 or more, and the substituents can be the same or different.

By the lower alkyl group in the definition of $R_1$ and $R_2$ is meant a linear or branched alkyl group having 1 to 6 carbon atoms, such as methyl, ethyl, n-propyl, isopropyl, n-pentyl, 1-ethylpropyl, isoamyl or n-hexyl group.

Typical examples of the compounds of formula [II] provided according to the present invention are as follows:

(1) 5-Phenyl-2-[3-(3,4-methylenedioxyphenyl)propionyl]-cyclohexane-1,3-dione
(2) 5-(4-Methoxyphenyl)-2-[3-(3,4-methylenedioxyphenyl)propionyl]-cyclohexane-1,3-dione
(3) 5-(2-Methoxyphenyl)-2-[3-(3,4-methylenedioxyphenyl)propionyl]-cyclohexane-1,3-dione
(4) 5-(4-Chlorophenyl)-2-[3-(3,4-methylenedioxyphenyl)propionyl]-cyclohexane-1,3-dione
(5) 5-(3,4-Dichlorophenyl)-2-[3(3,4-methylenedioxyphenyl)propionyl]-cyclohexane-1,3-dione
(6) 5-(2-Trifluoromethylphenyl)-2-[3-(3,4-methylenedioxyphenyl)propionyl]-cyclohexane-1,3-dione
(7) 5-(4-Tolyl)-2-[3-(3,4-methylenedioxyphenyl)propionyl]cyclohexane-1,3-dione
(8) 5-(3-Hydroxyphenyl)-2-[3-(3,4-methylenedioxyphenyl)propionyl]-cyclohexane-1,3-dione
(9) 5-(4-Hydroxyphenyl)-2-[3-(3,4-methylenedioxyphenyl)-propionyl]-cyclohexane-1,3-dione
(10) 5-(3,4-Dihydroxyphenyl)-2-[3-(3,4-methylenedioxyphenyl)-propionyl]-cyclohexane-1,3-dione
(11) 5-Phenyl-2-[3-(2,2-dimethyl-1,3-benzodioxol-5-yl)-propionyl]-cyclohexane-1,3-dione
(12) 5-Phenyl-2-[3-(2,2-diphenyl-1,3-benzodioxol-5-yl)-propionyl]-cyclohexane-1,3-dione
(13) 5-Phenyl-2-[3-(3,4-carbonyldioxyphenyl)-propionyl]-cyclohexane-1,3-dione
(14) 5-(4-Cumenyl)-2-[3-(3,4-methylenedioxyphenyl)-propionyl]-cyclohexane-1,3-dione
(15) 5-(4-Butoxyphenyl)-2-[3-(3,4-methylenedioxyphenyl)-propionyl]-cyclohexane-1,3-dione
(16) 5-(4-Dimethylaminophenyl)-2-[3-(3,4-methylenedioxyphenyl)-propionyl]-cyclohexane-1,3-dione
(17) 5-(4-Diethylaminophenyl)-2-[3-(3,4-methylenedioxyphenyl)-propionyl]-cycohexane-1,3-dione
(18) 5-(3,4-Ethylenedioxyphenyl)-2-[3-(3,4-methylenedioxyphenyl)-propionyl]-cyclohexane-1,3-dione
(19) 5-(3,4-Methylenedioxyphenyl)-2-[3-(3,4-methylenedioxyphenyl)-propionyl]-cyclohexane-1,3-dione

(20) 5-(2-Furyl)-2-[3-(3,4-methylenedioxyphenyl)-propionyl]-cyclohexane-1,3-dione
(21) 5-Phenyl-2-[3-(2,2-dipropyl-1,3-benzodioxol-5-yl)-propionyl]-cyclohexane-1,3-dione
(22) 5-Phenyl-2-[3-(2,2-diethyl-1,3-benzodioxol-5-yl)-propionyl]-cyclohexane-1,3-dione
(23) 5-Phenyl-2-[3-(2-ethyl-2-methyl-1,3-benzodioxol-5-yl)-propionyl]-cyclohexane-1,3-dione
(24) 5-Phenyl-2-[3-(3,4-ethylenedioxyphenyl)-propionyl]-cyclohexane-1,3-dione
(25) 5-Phenyl-2-(3,4-methylenedioxybenzoyl)-cyclohexane-1,3-dione
(26) 5-Phenyl-2-(3,4-methylenedioxyphenylacetyl)-cyclohexane-1,3-dione
(27) 5-(4-Tolyl)-2-(3,4-methylenedioxyphenylacetyl)-cyclohexane-1,3-dione
(28) 5-(2-Methoxyphenyl)-2-(3,4-methylenedioxyphenylacetyl)-cyclohexane-1,3-dione
(29) 5-Phenyl-2-[4-(3,4-methylenedioxyphenyl)-butyryl]-cyclohexane-1,3-dione
(30) 5-(4-Tolyl)-2-[4-(3,4-methylenedioxyphenyl)-butyryl]-cyclohexane-1,3-dione
(31) 5-(2-Methoxyphenyl)-2-[4-(3,4-methylenedioxyphenyl)-butyryl]-cyclohexane-1,3-dione
(32) 5-Phenyl-2-[5-(3,4-methylenedioxyphenyl)-valeryl]-cyclohexane-1,3-dione
(33) 5-(4-Tolyl)-2-[5-(3,4-methylenedioxyphenyl)-valeryl]-cyclohexane-1,3-dione
(34) 5-(2-Methoxyphenyl)-2-[5-(3,4-methylenedioxyphenyl)-valeryl]-cyclohexane-1,3-dione
(35) 5-(4-n-Butylphenyl)-2-[5-(3,4-methylenedioxyphenyl)-valeryl]-cyclohexane-1,3-dione.

The compounds of formula [II], according to the present invention, are considered to include various keto-type and enol-type compounds, for example, compounds represented by the following general formulae [II-a] and [II-b]:

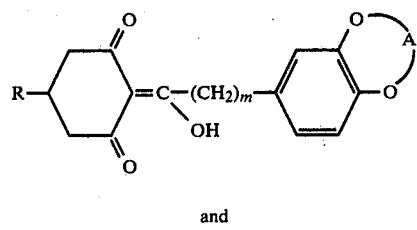

[II-a]

and

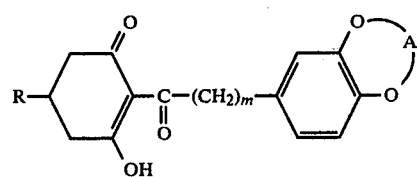

[II-b]

wherein R, m and A are as defined above. Since enol-type and keto-type compounds are substantially identical, these compounds are included in the scope of the present invention.

The other group of compounds within the scope of formula [I] is shown by the following formula [III]

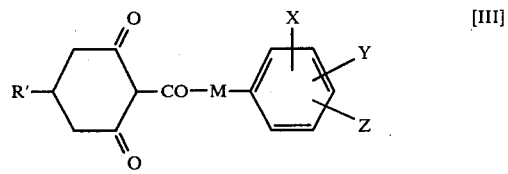

[III]

wherein R' stands for an unsubstituted or substituted phenyl group or a furyl group, M stands for a group represented by the formula $-(CH_2)_m-$ in which m is an integer of from 0 to 4 or a group represented by the formula $-NH-$, and X, Y and Z, which can be the same or different, stand for a hydrogen atom, a lower alkyl group, a lower alkoxy group, a lower alkyl-carbonyloxy group, a hydroxyl group, a lower alkyl-sulfonyl group, a nitro group, a cyano group or a halogen atom.

In the above general formula, R' stands for an unsubstituted or substituted phenyl group or a furyl group. As the substituent on the phenyl group, there can be mentioned, for example, linear and branched lower alkyl groups having 1 to 6 carbon atoms, such as methyl, ethyl, n-propyl, isopropyl, n-pentyl, 1-ethylpropyl, isoamyl and n-hexyl groups, lower alkoxy groups having 1 to 6 carbon atoms, such as methoxy, ethoxy, n-propoxy, isopropoxy, n-butoxy and isobutoxy groups, a hydroxyl group, halogen atoms such as chlorine, bromine, fluorine and iodine, halogenated alkyl groups such as a trifluoromethyl group, an amino group, substituted amino groups such as N,N-dimethylamino and N,N-diethylamino groups, and groups of the formula $-O-(CH_2)_a-O-$ in which a is an integer of 1 or 2, which group is bonded to any two adjacent carbon atoms of the phenyl group, such as methylenedioxy and ethylenedioxy groups. The number of the substituents is 1 or more, and the substituents can be the same or different.

X, Y and Z, which can be the same or different, stand for a hydrogen atom, a linear or branched lower alkyl group having 1 to 6 carbon atoms, such as a methyl, ethyl, n-propyl, isopropyl, n-penyl, 1-ethylpropyl, isoamyl or n-hexyl group, a lower alkoxy group having 1 to 6 carbon atoms, such as a methoxy, ethoxy, n-propoxy, isopropoxy, n-butoxy or isobutoxy group, a lower alkylcarbonyloxy group such as an acetoxy, propionyloxy or valeryloxy group, a hydroxyl group, a lower alkylsulfonyl group such as a methylsulfonyl, ethylsulfonyl, propylsulfonyl or butylsulfonyl group, a nitro group, a cyano group, or a halogen atom such as fluorine, chlorine, bromine or iodine.

Typical examples of the cyclohexane derivatives of the formula [III], according to the present invention, are as follows.

(51) 2-(3-Phenylpropionyl)-5-phenyl-cyclohexane-1,3-dione
(52) 2-[3-(2-Methoxyphenyl)-propionyl]-5-phenylcyclohexane-1,3-dione
(53) 2-[3-(3-Methoxyphenyl)-propionyl]-5-phenylcyclohexane-1,3-dione
(54) 2-[3-(4-Methoxyphenyl)-propionyl]-5-phenylcyclohexane-1,3-dione
(55) 2-[3-(3,4-Dimethoxyphenyl)-propionyl]-5-phenyl-cyclohexane-1,3-dione
(56) 2-[3-(2,3,4-Trimethoxyphenyl)-propionyl]-5-phenyl-cyclohexane-1,3-dione

(57) 2-[3-(4-Methylphenyl)-propionyl]-5-phenyl-cyclohexane-1,3-dione
(58) 2-[3-(2-Chlorophenyl)-propionyl]-5-phenyl-cyclohexane-1,3-dione
(59) 2-[3-(4-Chlorophenyl)-propionyl]-5-phenyl-cyclohexane-1,3-dione
(60) 2-[3-(2,4-Dichlorophenyl)-propionyl]-5-phenylcyclohexane-1,3-dione
(61) 2-[3-(4-Methylsulfonylphenyl)-propionyl]-5-phenyl-cyclohexane-1,3-dione
(62) 2-[3-(4-Cyanophenyl)-propionyl]-5-phenyl-cyclohexane-1,3-dione
(63) 2-[3-(4-Hydroxyphenyl)-propionyl]-5-phenyl-cyclohexane-1,3-dione
(64) 2-[3-(3-Hydroxyphenyl)-propionyl]-5-phenylcyclohexane-1,3-dione
(65) 2-[3-(3,4-Dihydroxyphenyl)-propionyl]-5-phenyl-cyclohexane-1,3-dione
(66) 2-[3-(2-Hydroxy-3-methoxyphenyl)-propionyl]-5-phenyl-cyclohexane-1,3-dione
(67) 2-[3-(3,4-Diacetoxyphenyl)-propionyl]-5-phenylcyclohexane-1,3-dione
(68) 2-[3-(2-Fluorophenyl)-propionyl]-5-phenyl-cyclohexane-1,3-dione
(69) 2-[3-(4-Ethoxyphenyl)-propionyl]-5-phenyl-cyclohexane-1,3-dione
(70) 2-[3-(4-Propoxyphenyl)-propionyl]-5-phenyl-cyclohexane-1,3-dione
(71) 2-[3-(4-Methoxyphenyl)-propionyl]-5-(4-methoxyphenyl)-cyclohexane-1,3-dione
(72) 2-[3-(4-Chlorophenyl)-propionyl]-5-(4-methoxyphenyl)-cyclohexane-1,3-dione
(73) 2-[3-(2-Chlorophenyl)-propionyl]-5-(4-methoxyphenyl)-cyclohexane-1,3-dione
(74) 2-[3-(3,4-Dihydroxyphenyl)-propionyl]-5-(4-methoxyphenyl)-cyclohexane-1,3-dione
(75) 2-(3-Phenylpropionyl)-5-(4-methoxyphenyl)-cyclohexane-1,3-dione
(76) 2-[3-(3,4-Dihydroxyphenyl)-propionyl]-5-(2-methoxyphenyl)-cyclohexane-1,3-dione
(77) 2-(3-Phenylpropionyl)-5-(2-methoxyphenyl)-cyclohexane-1,3-dione
(78) 2-[3-(2-Chlorophenyl)-propionyl]-5-(4-chlorophenyl)-cyclohexane-1,3-dione
(79) 2-[3-(2,3,4-Trimethoxyphenyl)-propionyl]-5-(4-chlorophenyl)-cyclohexane-1,3-dione
(80) 2-[3-(3,4-Dihydroxyphenyl)-propionyl]-5-(4-methylphenyl)-cyclohexane-1,3-dione
(81) 2-(3-Phenylpropionyl)-5-(4-methylphenyl)-cyclohexane-1,3-dione
(82) 2-[3-(2-Chlorophenyl)-propionyl]-5-(4-methylphenyl)-cyclohexane-1,3-dione
(83) 2-(3-Phenylpropionyl)-5-(3,4-methylenedioxyphenyl)-cyclohexane-1,3-dione
(84) 2-[3-(3,4-Dihydroxyphenyl)-propionyl]-5-(3,4-methylenedioxyphenyl)-cyclohexane-1,3-dione
(85) 2-(3-Phenylpropionyl)-5-(3-hydroxyphenyl)-cyclohexane-1,3-dione
(86) 2-[3-(3,4-Dihydroxyphenyl)-propionyl]-5-(3-hydroxyphenyl)-cyclohexane-1,3-dione
(87) 2-(3-Phenylpropionyl)-5-(4-hydroxyphenyl)-cyclohexane-1,3-dione
(88) 2-[3-(3,4-Dihydroxyphenyl)-propionyl]-5-(4-hydroxyphenyl)-cyclohexane-1,3-dione
(89) 2-(3-Phenylpropionyl)-5-(3,4-dihydroxyphenyl)-cyclohexane-1,3-dione
(90) 2-[3-(3,4-Dihydroxyphenyl)-propionyl]-5-(3,4-dihydroxyphenyl)-cyclohexane-1,3-dione
(91) 2-Phenylacetyl-5-phenyl-cyclohexane-1,3-dione
(92) 2-(4-Chlorophenylacetyl)-5-phenyl-cyclohexane-1,3-dione
(93) 2-(2-Chlorophenylacetyl)-5-phenyl-cyclohexane-1,3-dione
(94) 2-(2,4-Dichlorophenylacetyl)-5-phenyl-cyclohexane-1,3-dione
(95) 2-(4-Methoxyphenylacetyl)-5-phenyl-cyclohexane-1,3-dione
(96) 2-(4-Methylphenylacetyl)-5-phenyl-cyclohexane-1,3-dione
(97) 2-(2-Nitrophenylacetyl)-5-phenyl-cyclohexane-1,3-dione
(98) 2-(2-Methoxyphenylacetyl)-5-phenyl-cyclohexane-1,3-dione
(99) 2-(4-Benzyloxyphenylacetyl)-5-phenyl-cyclohexane-1,3-dione
(100) 2-(4-Hydroxyphenylacetyl)-5-phenyl-cyclohexane-1,3-dione
(101) 2-(2-Benzyloxyphenylacetyl)-5-phenyl-cyclohexane-1,3-dione
(102) 2-(2-Hydroxyphenylacetyl)-5-phenyl-cyclohexane-1,3-dione
(103) 2-(2,3,4-Trimethoxyphenylacetyl)-5-phenyl-cyclohexane-1,3-dione
(104) 2-(2-Benzyloxy-3-methoxyphenylacetyl)-5-phenyl-cyclohexane-1,3-dione
(105) 2-(2-Hydroxy-3-methoxyphenylacetyl)-5-phenyl-cyclohexane-1,3-dione
(106) 2-Phenylacetyl-5-(4-chlorophenyl)-cyclohexane-1,3-dione
(107) 2-(2,4-Dichlorophenylacetyl)-5-(4-chlorophenyl)-cyclohexane-1,3-dione
(108) 2-(4-Methoxyphenylacetyl)-5-(4-chlorophenyl)-cyclohexane-1,3-dione
(109) 2-(4-Methylphenylacetyl)-5-(4-chlorophenyl)-cyclohexane-1,3-dione
(110) 2-(2-Chlorophenylacetyl)-5-(4-chlorophenyl)-cyclohexane-1,3-dione
(111) 2-(2,4-Dichlorophenylacetyl)-5-(2-furyl)-cyclohexane-1,3-dione
(112) 2-(4-Chlorophenylacetyl)-5-(2-furyl)-cyclohexane-1,3-dione
(113) 2-(2-Chlorophenylacetyl)-5-(2-furyl)-cyclohexane-1,3-dione
(114) 2-(4-Methoxyphenylacetyl)-5-(2-furyl)-cyclohexane-1,3-dione
(115) 2-(4-Methylphenylacetyl)-5-(2-furyl)-cyclohexane-1,3-dione
(116) 2-(2-Nitrophenylacetyl)-5-(2-furyl)-cyclohexane-1,3-dione
(117) 2-(4-Chlorophenyl)carbamoyl-5-phenyl-cyclohexane-1,3-dione
(118) 2-(2-Chlorophenyl)carbamoyl-5-phenyl-cyclohexane-1,3-dione
(119) 2-(2-Fluorophenyl)carbamoyl-5-phenyl-cyclohexane-1,3-dione
(120) 2-(4-Fluorophenyl)carbamoyl-5-phenyl-cyclohexane-1,3-dione
(121) 2-(4-Chlorophenyl)carbamoyl-5-(4-chlorophenyl)-cyclohexane-1,3-dione
(122) 2-(2-Chlorophenyl)carbamoyl-5-(4-chlorophenyl)-cyclohexane-1,3-dione
(123) 2-(4-Fluorophenyl)carbamoyl-5-(4-chlorophenyl)-cyclohexane-1,3-dione
(124) 2-(4-Chlorophenyl)carbamoyl-5-furyl-cyclohexane-1,3-dione (125) 2-(2-Chlorophenyl)carbamoyl-5-furyl-cyclohexane-1,3-dione
(126) 2-(2-Fluorophenyl)carbamoyl-5-furyl-cyclohexane-1,3-dione
(127) 2-(4-Fluorophenyl)carbamoyl-5-furyl-cyclohexane-1,3-dione
(128) 2-Benzoyl-5-phenyl-cyclohexane-1,3-dione
(129) 2-(4-Chlorobenzoyl)-5-phenyl-cyclohexane-1,3-dione
(130) 2-(4-Phenylbutyryl)-5-phenyl-cyclohexane-1,3-dione
(131) 2-[4-(2,4-Dihydroxyphenyl)-butyryl]-5-phenylcyclohexane-1,3-dione
(132) 2-(5-Phenylvaleryl)-5-phenyl-cyclohexane-1,3-dione
(133) 2[5-(4-Methoxyphenyl)-valeryl]-5-phenyl-cyclohexane-1,3-dione
(134) 2-(3-Phenylpropionyl)-5-(3,4-dichlorophenyl)-cyclohexane-1,3-dione
(135) 2-(3-Phenylpropionyl)-5-(4-butoxyphenyl)-cyclohexane-1,3-dione
(136) 2-(3-Phenylpropionyl)-5-(4-dimethylaminophenyl)-cyclohexane-1,3-dione
(137) 2-(3-Phenylpropionyl)-5-(4-diethylaminophenyl)-cyclohexane-1,3-dione
(138) 2-(3-Phenylpropionyl)-5-(3,4-ethylenedioxyphenyl)-cyclohexane-1,3-dione
(139) 2-[3-(4-Ethylsulfonylphenyl)-propionyl]-5-phenylcyclohexane-1,3-dione The compounds of formula [III] provided according to the present invention are considered to include various keto-type and enol-type compounds, for example, compounds represented by the following general formulae [IIIa] and [IIIa']:

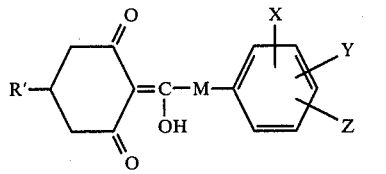

and

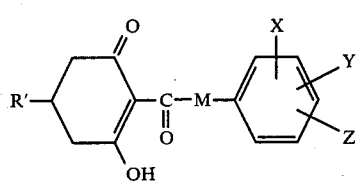

wherein R', M, X, Y and Z are as defined above. Since enol-type and keto-type compounds are substantially identical, these compounds are included in the scope of the present invention.

The pharmaceutically acceptable salts of the compounds of formula [I], according to the present invention, can be the customarily used non-toxic salts. For example, there can be mentioned alkali metal salts such as sodium and potassium salts, alkaline earth metal salts such as calcium and magnesium salts, iron salts, ammonium salts, and organic amine salts such as trimethylamine, triethylamine, ethanolamine, diethanolamine, pyridine and dicyclohexylamine salts.

Each of the cyclohexane derivatives provided according to the present invention is a novel compound not reported in any literature references. These cyclohexane derivatives are of low toxicity and they possess a very high hypotensive activity, and their antihypertensive effects are very long-lived.

The compounds of the present invention are very valuable for the prevention and treatment of various types of hypertension such as renal hypertension, endocrine hypertension, cardiovascular hypertension, nervous hypertension and essential hypertension.

Hypertension is a common adult disease and the number of persons suffering from hypertension has recently been increasing with the increase of the number of aged persons. However, since there are many causes of hypertension, although various antihypertensive agents have been proposed and used, no decisive medical treatment has been established. Because of the characteristics of this disease, patients suffering from hypertension should inevitably take antihypertensive agents continuously for a long period of time. Accordingly, it has been desired in the art to develop an antihypertensive agent which not only has a high medical effect, but also is excellent in the duration of the effect and has a high safety without causing any significant unwanted side effects.

We made researches with a view to developing antihypertensive agents satisfying these requirements and found that the compounds of the present invention have excellent pharmacological activities satisfying these requirements.

More specifically, the compounds of formula [I], according to the present invention, and salts thereof, exert a high hypotensive action gradually and reliably and they are excellent in the durability of the effect. Accordingly, they can be effectively and valuably used as antihypertensive agents. They are especially effective for treatment of essential hypertension, the cause of which is unknown.

Furthermore, the compounds of formula [I] of the present invention, and salts thereof, are valuable as antibiotic substances against Gram-positive bacteria, Gram-negative bacteria and true fungi.

The compounds of formula [II] of the present invention can be prepared by various processes. Examples of the preparation processes customarily employed will now be described.

(1) Preparation Process A

This process is represented by the following reaction scheme:

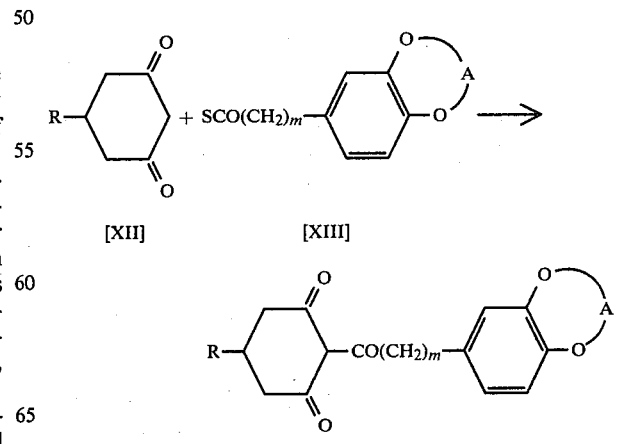

wherein X stands for a halogen atom, and R, A and m are the same as defined above.

Namely, a compound represented by the general formula [XII] is reacted with a compound represented by the general formula [XIII], thereby to obtain the desired compound [II] of the present invention.

This reaction can be carried out in the absence of a solvent or in the presence of a solvent which does not participate in the reaction, which solvent is appropriately selected from dimethylformamide, benzene type solvents such as benzene, toluene and xylene, and ether type solvents such as diethyl ether and tetrahydrofuran. The reaction progresses even at room temperature, but it is preferred that the temperature be elevated to the boiling point of the solvent used. If a catalyst such as triethylamine, an alkali metal bicarbonate, an alkali metal carbonate or pyridine is added to the reaction system, the reaction will progress very smoothly. It is preferred that the catalyst is used in an amount of at least 2 moles per mole of the starting substance.

(2) Preparation Process B

A compound of the general formula [II], in which m is 2 or 4, can be prepared also according to the process represented by the following reaction scheme:

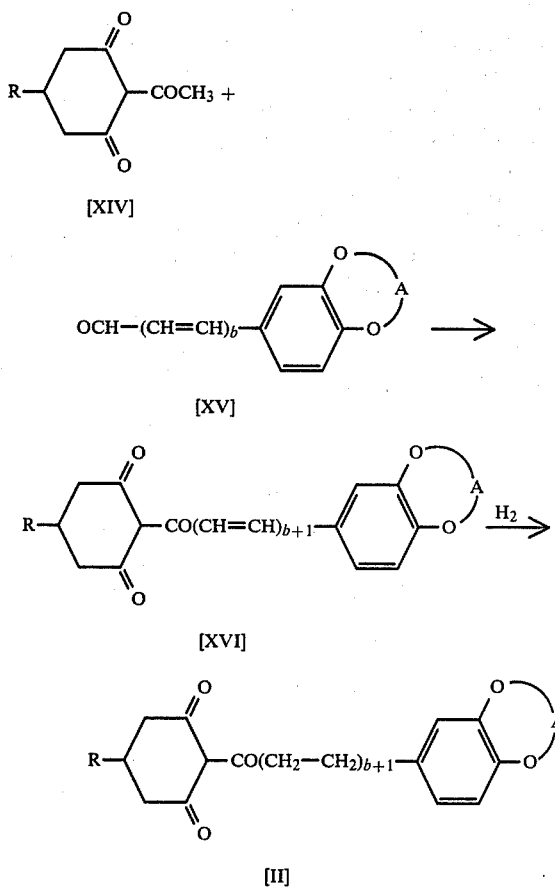

wherein R and A are the same as defined above, and b is zero or the integer 1.

More specifically, a compound represented by the general formula [XIV] is reacted with a compound represented by the general formula [XV] to obtain a compound represented by the general formula [XVI],
and the thus-obtained compound is reduced to obtain the desired compound [II] of the present invention.

The reaction of a compound represented by the general formula [XIV] with a compound represented by the general formula [XV] is carried out in the presence of a catalyst, for example, an acid such as hydrogen chloride or boron trifluoride or a base such as piperidine, morpholine, pyrrolidine or sodium hydroxide. This reaction can be carried out in the absence of a solvent or in the presence of a solvent that does not participate in the reaction, which solvent is appropriately selected from lower alcohols such as methanol, ethanol, propanol and isopropanol, benzene type solvents such as benzene, toluene and xylene, ether type solvents such as diethyl ether and tetrahydrofuran, and halogenated alkane type solvents such as chloroform and dichloroethane. The reaction progresses even at room temperature, but it is preferred that the temperature be elevated to the boiling point of the solvent used. If the water formed by the reaction is removed from the reaction system, the reaction will progress more smoothly.

When the desired compound [II] of the present invention is obtained by reducing with hydrogen the thus-obtained compound represented by the general formula [XVI], a solvent appropriately selected from alcohols, ethers and acetic acid is used, and reduction is carried out under atmospheric or elevated pressure, in the presence of a catalyst such as palladium, Raney nickel or platinum oxide, whereby the desired compound of formula [II] of the present invention is formed.

In this preparation process of the present invention, if a secondary amine such as piperidine, morpholine or pyrrolidine is used as the basic catalyst for the reaction of the compound of the formula [XIV] with the compound of the formula [XV], an enamine type compound is formed. More specifically, when a secondary amine such as one of those mentioned above is used, there is obtained an enamine type compound represented by the following general formula [XVII]:

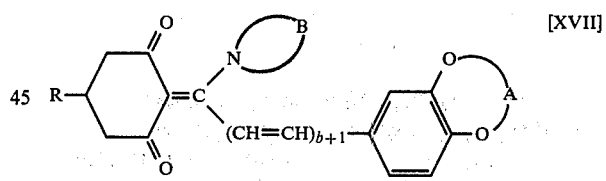

wherein R, A and b are the same as defined above, and B stands for a group represented by the formula $-(CH_2)_4-$, $-(CH_2)_5-$ or $-(CH_2)_2-O-(CH_2)_2-$. Also in this case, the desired compound [II] of the present invention can be obtained by reducing the compound [XVII] by the same procedure as described above.

(3) Preparation Process C

A compound of the general formula [II] in which A stands for a group

wherein $R_1$ and $R_2$ can be the same or different, and are a lower alkyl group or a phenyl group, can be prepared also by reacting a compound represented by the following general formula [XVIII]:

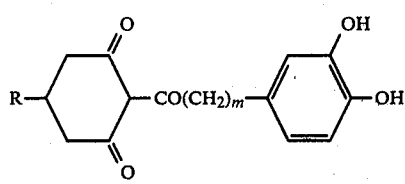

wherein R and m are the same as defined above, with a compound represented by the following general formula [XIX]:

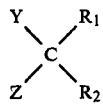

wherein $R_1$ and $R_2$ are the same as defined above, and Y and Z, which can be the same or different, stand for a lower alkyl group, a lower alkoxy group or a halogen atom.

Ordinarily, this reaction is carried out in the absence of a solvent or in the presence of an ether type solvent, a benzene type solvent or a halogen type solvent.

(4) Preparation Process D

A compound of the general formula [II] in which A stands for a group >C=O can be prepared also by reacting a compound of the general formula [XVIII], which is used in the preparation process C, with a compound represented by the following general formula [XX]:

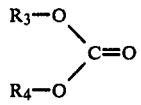

wherein $R_3$ and $R_4$, which can be the same or different, stand for an alkyl group or a phenyl group.

Ordinarily, this reaction is carried out in the absence of a solvent or in the presence of an ether type solvent, a benzene type solvent or a halogen type solvent.

The compound of formula [III] can be prepared in the following manner.

(5) Preparation Process E

The desired compound of the general formula [III] in which M stands for $-(CH_2)_m-$, that is, a compound represented by the following formula [IIIb]:

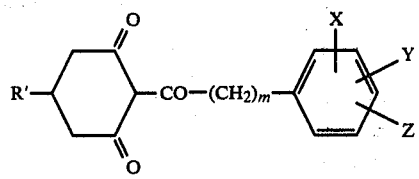

is prepared according to the process represented by the following reaction scheme:

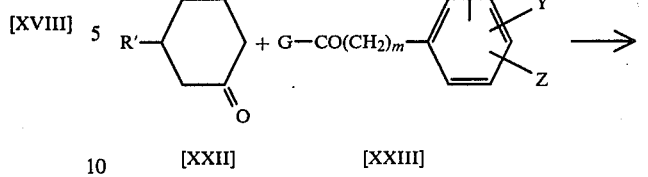

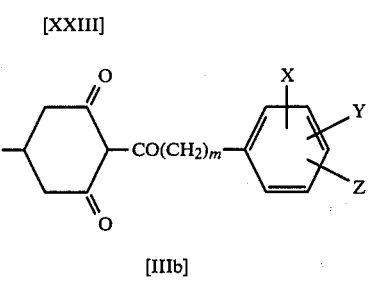

wherein G stands for a halogen atom, and R' and m are the same as defined above.

In short, a compound represented by the general formula [XXII] is reacted with a compound represented by the general formula [XXIII] to obtain the desired compound [IIIb] of the present invention.

This reaction can be carried out in the absence of a solvent or in the presence of a solvent that does not participate in the reaction, which solvent is appropriately selected from dimethylformamide, benzene type solvents such as benzene, toluene and xylene, ether type solvents such as diethyl ether and tetrahydrofuran, and halogen type solvents. The reaction progresses even at room temperature, but it is preferred that the temperature be elevated to the boiling point of the solvent used. If a catalyst such as triethylamine, an alkali metal bicarbonate, an alkali metal carbonate or pyridine is added to the reaction system, the reaction progresses very smoothly. It is preferred that the catalyst be used in an amount of at least 2 moles per mole of the starting substance.

(6) Preparation Process F

A compound of the general formula [IIIb] in which m is 2 or 4 can be prepared also according to the process represented by the following reaction scheme:

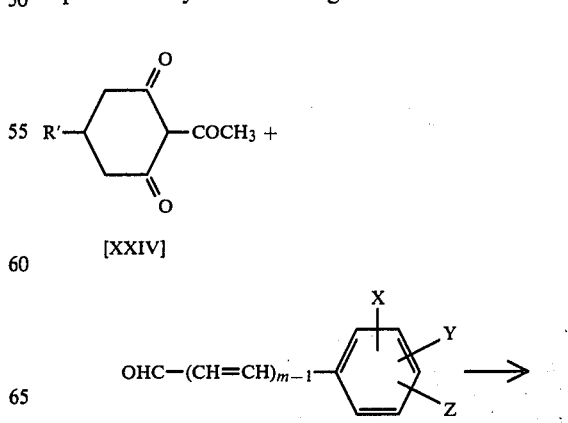

-continued

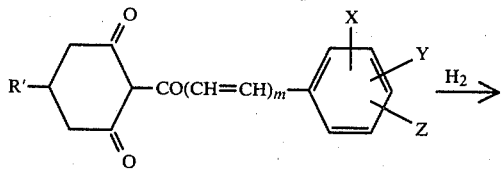

[XXVI]

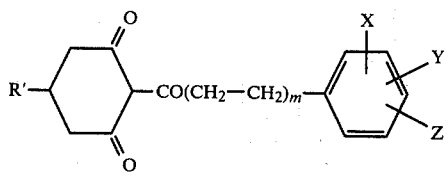

[IIIb]

wherein R', X, Y and Z are the same as defined above.

More specifically, a compound represented by the general formula [XXIV] is reacted with a compound represented by the general formula [XXV] to obtain a compound represented by the general formula [XXVI], and the thus-obtained compound is reduced to obtain the desired compound [IIIb] of the present invention.

The reaction of a compound represented by the general formula [XXIV] with a compound represented by the general formula [XXV] is carried out in the presence of a catalyst, for example, an acid such as hydrogen chloride or boron trifluoride or a base such as piperidine, morpholine, pyrrolidine or sodium hydroxide, or a mixture thereof. This reaction may be carried out in the absence of a solvent or in the presence of a solvent that does not participate in the reaction, which solvent is appropriately selected from lower alcohols such as methanol, ethanol, propanol and isopropanol, benzene type solvents such as benzene, toluene and xylene, ether type solvents such as diethyl ether and tetrahydrofuran, and halogenated alkane type solvents such as chloroform and dichloroethane. The reaction progresses even at room temperature, but it is preferred that the temperature be elevated to the boiling point of the solvent used. If the water formed by the reaction is removed from the reaction system, the reaction progresses more smoothly.

When the desired compound [IIIb] of the present invention is obtained by reducing the thus-obtained compound represented by the general formula [XXVI], a solvent appropriately selected from alcohols, ethers and acetic acid is used, and reduction is carried out under atmospheric or elevated pressure in the presence of a catalyst such as palladium, Raney nickel or platinum oxide, whereby an intended compound [IIIb] of the present invention is formed.

In this preparation process of the present invention, if a secondary amine such as piperidine, morpholine or pyrrolidine is used as the basic catalyst for the reaction of the compound of the formula [XXIV] with the compound of the formula [XXV], an enamine type compound is formed. More specifically, when a secondary amine such as those mentioned above is used, there is obtained an enamine type compound represented by the following general formula [XXVII]:

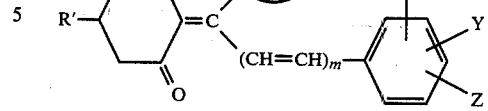

[XXVII]

wherein R', X, Y, Z and m are the same as defined above, and B stands for a group represented by the formula —(CH$_2$)$_4$—, —(CH$_2$)$_5$— or —(CH$_2$)$_2$—O—(CH$_2$)$_2$—. Also in this case, the desired compound [IIIb] of the present invention can be obtained by reducing the compound [XXVII] by the same procedures as described above.

(7) Preparation Process G

The desired compound of the present invention represented by the general formula [III] in which m is the group —NH—, that is, a compound represented by the following formula [IIIc]:

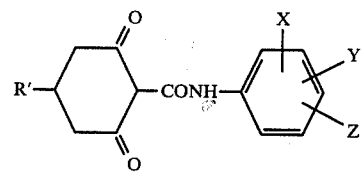

[IIIc]

can be prepared according to the process represented by the following reaction scheme:

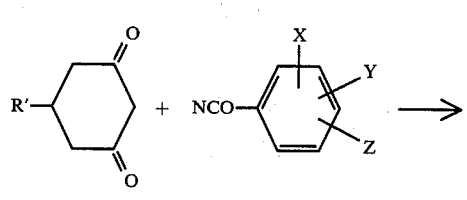

[XXII]    [XXVIII]

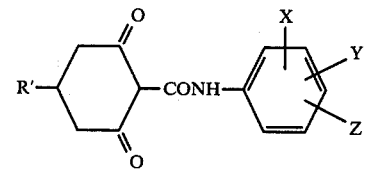

[IIIc]

wherein R', X, Y and Z are the same as defined above.

More specifically, the desired compound [IIIc] of the present invention is obtained by reacting a compound of the general formula [XXII] with a compound of the general formula [XXVIII].

The reaction can be carried out in the absence of a solvent or in the presence of a solvent that does not participate in the reaction, which solvent is appropriately selected from dimethylformamide, benzene type solvents such as benzene, toluene and xylene and ether type solvents such as diethyl ether and tetrahydrofuran. The reaction progresses even at room temperature but it is preferred that the temperature be elevated to the boiling point of the solvent used. If a catalyst such as triethylamine, an alkali metal bicarbonate, an alkali metal carbonate or pyridine is added to the reaction system, the reaction progresses more smoothly.

The excellent pharmacological activities of the compounds of the present invention will now be described with reference to typical examples thereof.

1. Hypotensive Action

A test compound suspended in a gum arabic solution was orally administered once a day, at a dose of 10 mg/Kg (body weight), for 2 days, to groups of spontaneous hypertensive rats (hereinafter referred to as "SHR") (about 30 weeks old; systolic pressure=about 230 mm Hg), each group consisting of 6 rats.

The systolic pressure was measured from the tail artery of SHR under no anesthesia before the administration and 6 hours after the time of administration by using a continuous tonometer (Shimazu Tonometer Model SCS-301 manufactured by Shimazu Seisakusho K.K.). An aqueous solution of gum arabic alone was administered to the rats of the control group.

The obtained results as to the compounds [II] and [III] are shown in Table 1.

TABLE 1

Blood Pressures on Administration of 10 mg/Kg for 2 Days

| Test Compound | Blood Pressure (mm Hg) on First Day | | Blood Pressure (mm Hg) on Second Day | | |
|---|---|---|---|---|---|
| | before administration | after 6 hours | before administration | after 6 hours | after 24 hours |
| (phenyl-cyclohexanedione-COCH$_2$CH$_2$-methylenedioxyphenyl) | 231 ± 4 | *205 ± 7 | 218 ± 7 | *204 ± 6 | *207 ± 7 |
| (4-methylphenyl-cyclohexanedione-COCH$_2$CH$_2$-methylenedioxyphenyl) | 232 ± 5 | *198 ± 5 | *200 ± 10 | *188 ± 5 | *192 ± 5 |
| (2-methoxyphenyl-cyclohexanedione-COCH$_2$CH$_2$-methylenedioxyphenyl) | 232 ± 6 | *210 ± 5 | 220 ± 6 | *205 ± 5 | 220 ± 6 |
| (phenyl-cyclohexanedione-COCH$_2$CH$_2$-(dimethyl-dioxyphenyl)) | 228 ± 7 | *207 ± 3 | 202 ± 7 | *190 ± 5 | *192 ± 7 |
| (phenyl-cyclohexanedione-COCH$_2$CH$_2$-(diphenyl-dioxyphenyl)) | 232 ± 5 | *202 ± 5 | 210 ± 10 | *192 ± 5 | *208 ± 5 |
| (phenyl-cyclohexanedione-COCH$_2$CH$_2$-(4-methoxyphenyl)) | 232 ± 5 | *209 ± 5 | 213 ± 6 | *210 ± 5 | 212 ± 6 |

TABLE 1-continued

| | Blood Pressures on Administration of 10 mg/Kg for 2 Days | | | | |
|---|---|---|---|---|---|
| | Blood Pressure (mm Hg) on First Day | | Blood Pressure (mm Hg) on Second Day | | |
| Test Compound | before administration | after 6 hours | before administration | after 6 hours | after 24 hours |
| 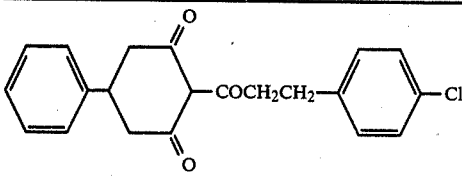 | 235 ± 2 | *198 ± 8 | *195 ± 5 | *210 ± 5 | 215 ± 8 |
| 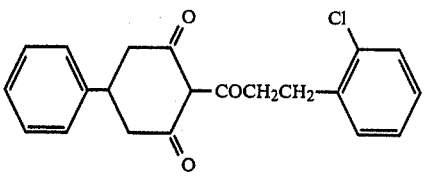 | 240 ± 5 | *200 ± 3 | *208 ± 9 | *213 ± 4 | *193 ± 1 |
| 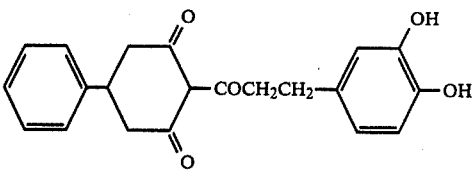 | 231 ± 6 | *204 ± 5 | *209 ± 5 | *200 ± 5 | *205 ± 5 |
| 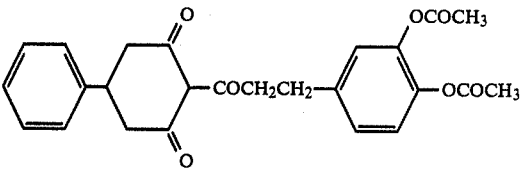 | 230 ± 1 | *195 ± 10 | 222 ± 5 | *195 ± 10 | *212 ± 5 |
| 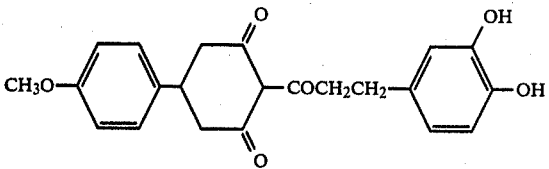 | 235 ± 5 | *212 ± 3 | 225 ± 1 | 220 ± 1 | 228 ± 2 |
| 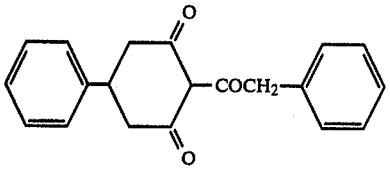 | 233 ± 5 | *183 ± 3 | *203 ± 3 | *183 ± 3 | *193 ± 7 |
| 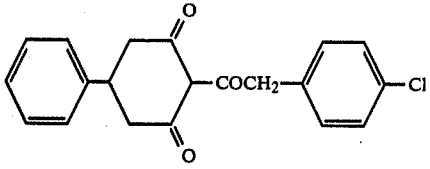 | 236 ± 6 | *215 ± 1 | 217 ± 4 | *215 ± 2 | 222 ± 4 |
| Control | 234 ± 5 | 234 ± 4 | 234 ± 5 | 234 ± 4 | 234 ± 4 |

Note
*There was observed a significant difference between the control group and the test compound-administered group in the measurement of the reduction of the blood pressure (significance level P = 0.01).

As will be apparent from the results shown in Table 1, in each of the series of compounds according to the present invention, an apparent reduction of the blood pressure is observed 6 hours after the time of administration, but in the control group, the blood pressure of 245±5 mm Hg before the test is not appreciably changed during the test period of 2 days. Thus, it will readily be understood that the compounds of the present invention have an excellent hypotensive action and they are valuable as antihypertensive agents, especially for treating essential hypertension.

2. Acute Toxicity

Groups of rats of the SD series (body weight = 160–280 g; about 8 weeks old), each group consisting of 5 rats, were used. After administration of the test compound, the death or survival was examined during a period of 14 days to determine the $LD_{50}$ value. The obtained results are shown in Table 2.

TABLE 2

| | $LD_{50}$ Values | | | |
| --- | --- | --- | --- | --- |
| | Oral Administration | | Abdominal Administration | |
| Test Compound | male | female | male | female |
| 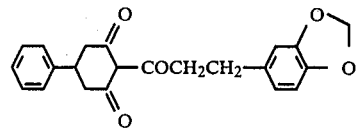 | >4000 | >4000 | >500 | >500 |
| 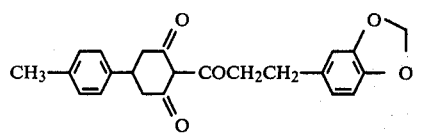 | >4000 | >4000 | >500 | >500 |
| 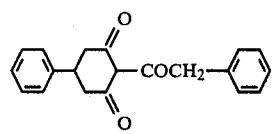 | >4000 | >4000 | >500 | >500 |

The present invention will now be described in detail with reference to the following illustrative Examples that by no means limit the scope of the present invention.

EXAMPLE 1

Synthesis of 5-phenyl-2-[3-(3,4-methylenedioxyphenyl)-propionyl]-cyclohexane-1,3-dione (1) Preparation of 5-phenyl-2-[3-(3,4-methylenedioxyphenyl)-propenoyl]-cyclohexane-1,3-dione To 150 ml of benzene were added 23 g of 2-acetyl-5-phenyl-cyclohexane-1,3-dione, 21 g of piperonal and 14 ml of morpholine, and the mixture was stirred under reflux while the water formed by the reaction was removed by distillation. Then, 200 ml of chloroform was added to the reaction mixture, and the mixture was washed with 100 ml of 0.5 N hydrochloric acid 2 times, then washed with water and dried with magnesium sulfate. The solvent was removed by distillation and the obtained crude crystals were recrystallized from ethanol to obtain 18.5 g (the yield being 51%) of 5-phenyl-2-[3-(3,4-methylenedioxyphenyl)-propenoyl]-cyclohexane-1,3-dione having a melting point of 157° to 158° C.

(2) Preparation of 5-phenyl-2-[3-(3,4-methylenedioxyphenyl)-propionyl]-cyclohexane-1,3-dione In 200 ml of tetrahydrofuran was dissolved 10.8 g of 5-phenyl-2-[3-(3,4-methylenedioxyphenyl)-propenoyl]-cyclohexane-1,3-dione prepared in step (1) above, and 2 g of a 5% palladium-carbon catalyst was added to the solution and catalytic reduction was carried out for 7 hours with hydrogen under atmospheric pressure. The catalyst was removed by filtration and tetrahydrofuran was removed by distillation. Recrystallization from isopropyl alcohol have 7.5 g (the yield being 70%) of the desired 5-phenyl-2-[3-(3,4-methylenedioxyphenyl)-propionyl]-cyclohexane-1,3-dione.

Melting Point: 109°–110° C.

Elementary Analysis Values as $C_{22}H_{20}O_5$: Calculated: C=72.51%, H=5.53%; Found: C=72.98%, H=5.62%.

IR (cm$^{-1}$, nujol): 1662, 1550, 1241, 922.

NMR ($\delta$, CDCl$_3$): 2.6–3.5 (9H, m), 5.84 (2H, s), 6.65 (3H, m), 7.25 (5H, m), 18.04 (1H, s) (disappeared at D$_2$O).

EXAMPLE 2

Synthesis of 5-(3,4-methylenedioxyphenyl)-2-[3-(3,4-methylenedioxyphenyl)-propionyl]-cyclohexane-1,3-dione (1) Preparation of 5-(3,4-methylenedioxyphenyl)-2-[3-(3,4-methylenedioxyphenyl)-propenoyl]-cyclohexane-1,3-dione To 50 ml of toluene was added 2.7 g of 2-acetyl-5-(3,4-methylenedioxyphenyl)-cyclohexane-1,3-dione, 1.8 g of piperonal and 1.8 g of morpholine, and the mixture was stirred under reflux for 7 hours while the water formed by the reaction was removed by azeotropic distillation. The reaction mixture was allowed to stand still overnight, and the crystals were recovered by filtration to obtain 2.44 g (the yield being 49%) of an enamine type adduct compound, that is, 5-(3,4-methylenedioxyphenyl)-2-[3-(3,4-methylenedioxyphenyl)-1-morpholinoallylidene]-cyclohexane-1,3-dione having a melting point of 216°–219° C.

The filtrate left after recovery of the crystals was concentrated and extracted with chloroform, and the chloroform layer was washed with water and then dried. The solvent was removed by distillation and crude crystals were recovered by silica gel column chromatographic separation. Recrystallization from benzene/ethanol gave 0.38 g (the yield being 9.1%) of 5-(3,4-methylenedioxyphenyl)-2-[3-(3,4-methylenedioxyphenyl)-propenoyl]-cyclohexane-1,3-dione.

(2) Preparation of 5-(3,4-methylenedioxyphenyl)-2-[3-(3,4-methylenedioxyphenyl)-propionyl]-cyclohexane-1,3-dione In 80 ml of acetic acid was dissolved 0.5 g of 5-(3,4-methylenedioxyphenyl)-2-[3-(3,4-methylenedioxyphenyl)-propenoyl]-cyclohexane-1,3-dione prepared in step (1) above, and 0.5 g of a 5% palladium-carbon catalyst was added to the solution and catalytic reduction was carried out with hydrogen under atmospheric pressure for 4 hours. The catalyst was removed and the residue was crystallized from isopropyl alcohol and recrystallized from ethanol to obtain 0.32 g (the yield being 64%) of the desired 5-(3,4-methylenedioxyphenyl)-2-[3-(3,4-methylenedioxyphenyl)-propionyl]-cyclohexane-1,3-dione.

Melting Point: 108°–109° C.

Elementary Analysis Values as $C_{23}H_{20}O_7$: Calculated: C=67.64%, H=4.94%; Found: C=67.56%, H=5.01%.

IR ($cm^{-1}$, nujol): 1662, 1560, 1240, 925.

NMR ($\delta$, $CDCl_3$): 2.5–3.5 (9H, m), 5.87 (2H, s), 5.90 (2H, s), 6.16 (6H, s), 18.08 (1H, s) (disappeared at $D_2O$).

Similarly, 1.0 g of the above-mentioned enamine type adduct compound, that is, 5-(3,4-methylenedioxyphenyl)-2-[3-(3,4-methylenedioxyphenyl)-1-morpholinoallylidene]-cyclohexane-1,3-dione, was dissolved in 80 ml of acetic acid, and 0.5 g of a 5% palladium-carbon catalyst and 30 ml of deionized water were added to the solution and catalytic reduction was carried out with hydrogen under atmospheric pressure for 4 hours to obtain 0.38 g (the yield being 44%) of the desired compound.

EXAMPLE 3

Synthesis of 5-phenyl-2-[3-(2,2-dimethyl-1,3-benzodioxol-5-yl)-propionyl]-cyclohexane-1,3-dione To 50 ml of benzene was added 1 g of 5-phenyl-2-[3-(3,4-dihydroxyphenyl)-propionyl]-cyclohexane-1,3-dione (Example 15), and 0.33 g of 2,2-dimethoxypropane and 0.02 g of p-toluene-sulfonic acid were further added. The mixture was stirred under reflux for 1 hour. The reaction mixture was cooled, washed with water and dried with magnesium sulfate, and the solvent was removed by distillation and the residue was recrystalized from n-propyl alcohol to obtain 0.8 g (the yield being 68%) of the desired 5-phenyl-2-[3-(2,2-dimethyl-1,3-benzodioxol-5-yl)-propionyl]-cyclohexane-1,3-dione.

Melting Point: 144°–145° C.

Elementary Analysis Values as $C_{24}H_{24}O_5$: Calculated: C=73.45%, H=6.16%; Found: C=73.55%, H=6.29%.

IR ($cm^{-1}$, nujol): 1665, 1560, 1497.

NMR ($\delta$, $CDCl_3$): 1.62 (6H, s), 2.5–3.5 (9H, m), 6.67 (3H, s), 7.27 (5H, s), 18.06 (1H, s) (disappeared at $D_2O$).

EXAMPLE 4

Synthesis of 5-phenyl-2-[3-(2,2-diphenyl-1,3-benzodioxol-5-yl)-propionyl]-cyclohexane-1,3-dione In 30 ml of diglyme was dissolved 1 g of 5-phenyl-2-[3-(3,4-dihydroxyphenyl)-propionyl]-cyclohexane-1,3-dione, and 0.5 g of $\alpha,\alpha'$-dichlorodiphenylmethane was added and the mixture was refluxed for 3 hours on an oil bath. The reaction mixture was cooled, poured into water and extracted with 50 ml of benzene. The benzene extract was washed with water and dried with magnesium sulfate. Benzene was removed by distillation and the residue was recrystallized from n-propyl alcohol to obtain 0.8 g (the yield being 55%) of the desired 5-phenyl-2-[3-(2,2-diphenyl-1,3-benzodioxol-5-yl)-propionyl]-cyclohexane-1,3-dione.

Melting Point: 126° C.

Elementary Analysis Values as $C_{34}H_{28}O_5$: Calculated: C=79.05%, H=5.46%; Found: C=79.26%, H=5.77%.

IR ($cm^{-1}$, nujol): 1662, 1545, 1495, 1224.

NMR ($\delta$, $CDCl_3$): 2.5–3.55 (9H, m), 6.76 (2H, s), 6.97 (1H, s), 7.2–7.78 (15H, m) 18.1 (1H, s) (disappeared at $D_2O$).

EXAMPLE 5

Synthesis of 5-phenyl-2-[3-(3,4-carbonyldioxyphenyl)-propionyl]-cyclohexane-1,3-dione In 15 ml of diglyme was dissolved 1 g of 5-phenyl-2-[3-(3,4-dihydroxyphenyl)-propionyl]-cyclohexane-1,3-dione, and 0.7 g of diphenyl carbonate was added to the solution and reaction was carried out at 140° to 150° C. on an oil bath for 3 hours. The reaction mixture was cooled, poured into water and extracted with 50 ml of benzene. The benzene extract was washed with water and dried with magnesium sulfate. Benzene was removed by distillation and the residue was recrystallized from ethanol to obtain 0.5 g (the yield being 44%) of the desired 5-phenyl-2-[3-(3,4-carbonyldioxyphenyl)propionyl]-cyclohexane-1,3-dione.

Melting Point: 97.5°–98° C.

Elementary Analysis Values as $C_{22}H_{18}O_6$: Calculated: C=67.91%, H=5.70%; Found: C=68.05%, H=5.75%.

IR ($cm^{-1}$, nujol): 1764, 1660, 1550, 1245.

NMR ($\delta$, $CDCl_3$): 2.6–3.55 (9H, m), 6.85–7.3 (8H, m), 8.10 (1H, s) (disappeared at $D_2O$).

EXAMPLE 6

Synthesis of 5-phenyl-2-(3,4-methylenedioxyphenylacetyl)-cyclohexane-1,3-dione

In 70 ml of dry dimethylformamide was dissolved 7.5 g of 5-phenylcyclohexane-1,3-dione, and 9 ml of triethylamine was added to the solution. Then, 8.8 g of 3,4-methylenedioxyphenylacetyl chloride was added dropwise to the mixture under ice cooling (−10° C.), and the mixture was agitated at room temperature for 30 minutes. The reaction mixture was poured into 200 ml of 2 N hydrochloric acid and extracted with 100 ml of benzene. The benzene extract was washed with water and dried with magnesium sulfate. Benzene was removed by distillation and the residue was purified by silica gel chromatography and recrystallized from n-propanol to obtain 3.8 g (the yield being 27%) of the desired 5-phenyl-2-(3,4-methylenedioxyphenylacetyl)-cyclohexane-1,3-dione.

Melting Point: 104°–105° C.

Elementary Analysis Values as $C_{21}H_{18}O_5$: Calculated: C=71.99%, H=5.18%; Found: C=72.10%, H=5.10%.

IR ($cm^{-1}$, nujol): 1662, 1564, 1500, 1248, 1039.

NMR ($\delta$, $CDCl_3$): 2.5–3.5 (5H, m), 4.29 (2H, s), 5.84 (2H, s), 6.71 (3H, m), 7.22 (5H, m), 17.94 (1H, s). (disappeared at $D_2O$).

EXAMPLES 7 through 14

The compounds shown in Table 3 were synthesized according to the procedures described in Example 1.

TABLE 3

General structure:

R—(cyclohexane-1,3-dione)—CO(CH$_2$)$_m$—(benzo-dioxy-A ring)

| Example No. | m | R | A | Melting Point (°C.) | Molecular Formula | Elementary Analysis Values (%) (upper: calc., lower: found) C | H | IR (cm$^{-1}$ nujol) | NMR (δ, CDCl$_3$) |
|---|---|---|---|---|---|---|---|---|---|
| 7 | 2 | H | —CH$_2$— | 74.5 | C$_{16}$H$_{16}$O$_5$ | 66.66 / 66.65 | 5.59 / 5.79 | 1658, 1545, 1602, 1204, 1027 | 1.95(2H,m), 2.35–3.45(8H,m), 5.86(2H,s), 6.65(3H,m), 18.10(1H,s)(disappeared at D$_2$O) |
| 8 | 2 | CH$_3$O—C$_6$H$_4$— | —CH$_2$— | 97.5 | C$_{23}$H$_{22}$O$_6$ | 70.04 / 69.76 | 5.62 / 5.58 | 1663, 1550, 1243, 1040 | 2.5–3.5(9H,m), 3.75(3H,s), 5.83(2H,s), 6.65(3H,m), 6.78(2H,d,J=9Hz), 7.06(2H,d,J=9Hz), 18.12(1H,s)(disappeared at D$_2$O) |
| 9 | 2 | 2-OCH$_3$—C$_6$H$_4$— | —CH$_2$— | 95 | C$_{23}$H$_{22}$O$_6$ | 70.04 / 70.01 | 5.62 / 5.66 | 1661, 1540, 1242, 1037 | 2.6–3.6(9H,m), 3.84(3H,s), 5.92(2H,s), 6.7–7.45(7H,m), 18.10(1H,s)(disappeared at D$_2$O) |
| 10 | 2 | Cl—C$_6$H$_4$— | —CH$_2$— | 99.5–100 | C$_{22}$H$_{19}$ClO$_5$ | 66.25 / 66.42 | 4.80 / 4.73 | 1663, 1550, 1500, 1242, 1041 | 2.55–3.5(9H,m), 5.85(2H,s), 6.28(3H,m), 7.06(2H,d,J=9Hz), 7.31(2H,d,J=9Hz), 18.12(1H,s)(disappeared at D$_2$O) |
| 11 | 2 | CH$_3$—C$_6$H$_4$— | —CH$_2$— | 91.5 | C$_{23}$H$_{22}$O$_5$ | 73.66 / 72.96 | 5.86 / 5.81 | 1664, 1550, 1243, 1040 | 2.35(3H,s), 2.5–3.5(9H,m), 5.88(2H,s), 6.74(3H,m), 7.14(4H,s), 18.13(1H,s)(disappeared at D$_2$O) |
| 12 | 2 | 3-HO—C$_6$H$_4$— | —CH$_2$— | 119–120 | C$_{22}$H$_{20}$O$_6$ | 69.46 / 69.53 | 5.30 / 5.24 | 3370, 1647, 1547, 1502, 1223, 1036 | 2.6–3.4(9H,m), 5.87(2H,s), 6.5–7.1(7H,m), 9.37(1H,s), (disappeared at D$_2$O) |
| 13 | 2 | HO—C$_6$H$_4$— | —CH$_2$— | 152–153 | C$_{22}$H$_{20}$O$_6$ | 69.46 / 69.63 | 5.30 / 5.36 | 3200, 1640, 1540, 1245, 1040 | 2.6–3.4(9H,m), 5.87(2H,s), 6.5–6.8(5H,m), 7.06(2H,d,J=8Hz), 9.25(1H,s)(disappeared at D$_2$O) |

TABLE 3-continued

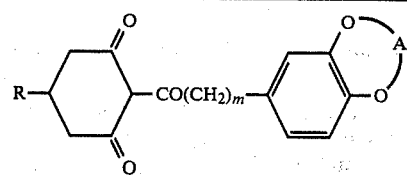

| Example No. | m | R | A | Melting Point (°C.) | Molecular Formula | Elementary Analysis Values (%) (upper value: calculated value, lower value: found value) | | IR (cm$^{-1}$ nujol) | NMR (δ, CDCl$_3$) |
|---|---|---|---|---|---|---|---|---|---|
| | | | | | | C | H | | |
| 14 | 2 |  | —CH$_2$— | 209–210 | C$_{22}$H$_{20}$O$_7$ | 66.66 / 66.68 | 5.09 / 5.10 | 3475, 3150, 1635, 1520, 1252 | 2.6–3.5(9H,m), 5.86(2H,s), 6.5–6.8(6H,m), 8.71(2H,s), (disappeared at D$_2$O) |

EXAMPLE 15

Synthesis of 2-[3-(3,4-dihydroxyphenyl)-propionyl]-5-phenyl-cyclohexane-1,3-dione In 100 ml of tetrahydrofuran was dissolved 4 g of 2-[3-(3,4-dibenzyloxyphenyl)-propenoyl]-5-phenyl-cyclohexane-1,3-dione, and 3 g of a 3% palladium-carbon catalyst was added to the solution and catalytic reduction was carried out with hydrogen under atmospheric pressure.

The catalyst was removed by filtration, and recrystallization from n-propyl alcohol/petroleum ether gave 1.2 g (the yield being 45%) of the desired 2-[3-(3,4-dihydroxyphenyl)-propionyl]-5-phenyl-cyclohexane-1,3-dione.

Melting Point: 225°–226° C.

Elementary Analysis Values as C$_{21}$H$_{20}$O$_5$: Calculated: C=71.58%, H=5.72%; Found: C=71.51%, H=5.83%.

IR (cm$^{-1}$, nujol): 3510, 1640, 1540.

NMR (δ, brom TMS): 2.6–3.4 (9H, m), 6.3–6.65 (3H, m), 7.28 (5H, s), 8.53 (1H, s), 8.64 (1H, s), 17.95 (1H, s) (disappeared at D$_2$O).

EXAMPLE 16

Synthesis of 2-phenylacetyl-5-phenyl-cyclohexane-1,3-dione

In 30 ml of dry dimethylformaldehyde was dissolved 1.9 g of 5-phenyl-cyclohexane-1,3-dione, and 3.4 ml of triethylamine was then added to the solution. Then, 1.7 g of phenylacetyl chloride was added dropwise to the mixture under ice cooling (0° C.).

After completion of the dropwise addition, the mixture was agitated at room temperature for 30 minutes and the reaction mixture was poured into 100 ml of water and the pH value was adjusted to 2 to 3 by 2 N hydrochloric acid. Then, the mixture was extracted with benzene, and the benzene extract was treated by silica gel chromatography (benzene was used as the solvent). Recrystallization from isopropyl alcohol gave 0.8 g (the yield being 26%) of the desired 2-phenylacetyl-5-phenyl-cyclohexane-1,3-dione.

Melting Point: 100°–100.5° C.

Elementary Analysis Values as C$_{20}$H$_{18}$O$_3$: Calculated: C=78.41%, H=5.92% Found: C=79.01%, H=6.13%.

IR (cm$^{-1}$, nujol): 1665, 1560, 1500, 1295.

NMR (δ, brom TMS): 2.6–3.6 (5H, m), 4.38 (2H, s), 7.27 (10H, s), 17.96 (1H, s) (disappeared at D$_2$O).

EXAMPLE 17

Synthesis of 2-(4-benzyloxyphenylacetyl)-5-phenyl-cyclohexane-1,3-dione

In 150 ml of dry dimethylformamide was dissolved 9.4 g of 5-phenyl-cyclohexane-1,3-dione, and 10 ml of triethylamine was added to the solution and 1.6 g of 4-benzyloxyphenylacetyl chloride was added dropwise to the mixture under ice cooling (−5° C.).

After completion of the dropwise addition, the mixture was agitated at room temperature for 30 minutes and 150 ml of benzene was added to the mixture. Then, the mixture was added to 200 ml of 2 N hydrochloric acid and agitated at room temperature for 30 minutes. The benzene layer was separated, extracted with 100 ml of benzene 2 times, washed with water, dried with magnesium sulfate and subjected to distillation. Separation by silica gel chromatography (benzene was used as the solvent) and recrystallization from n-propyl alcohol gave 3.4 g (the yield being 18%) of the desired 2-(4-benzyloxyphenylacetyl)-5-phenyl-cyclohexane-1,3-dione.

Melting Point: 115°–116° C.

Elementary Analysis Values as C$_{27}$H$_{24}$O$_4$: Calculated: C=78.62%, H=5.86%; Found: C=78.72%, H=5.83%.

IR (cm$^{-1}$, nujol): 1665, 1560, 1515, 1253.

NMR (δ, Brom TMS): 2.55–3.6 (5H, m), 4.33 (2H, s), 5.0 (2H, s), 6.86 (2H, d, J=9 Hz), 7.1–7.4 (12H, m), 17.96 (1H, s), (disappeared at D$_2$O).

EXAMPLE 18

Synthesis of 2-(4-hydroxyphenylacetyl)-5-phenyl-cyclohexane-1,3-dione

In 80 ml of tetrahydrofuran was dissolved 2 g of 2-(4-benzyloxyphenylacetyl)-5-phenyl-cyclohexane-1,3-dione, and 1 g of a 5% palladium-carbon catalyst was added to the solution and catalytic reduction was carried out at room temperature with hydrogen under atmospheric pressure for 4 hours. The catalyst was removed by filtration and the filtrate was concentrated and recrystallized from benzene. Column separation and recrystallization from benzene gave 0.8 g (the yield being 51%) of the desired 2-(4-hydroxyphenylacetyl)-5-phenyl-cyclohexane-1,3-dione.

Melting Point: 168°–168.5° C.

Elementary Analysis Values as $C_{20}H_{15}O_4$: Calculated: C=74.52%, H=5.63%; Found: C=74.62%, H=5.93%.

IR (cm$^{-1}$, nujol): 3190, 1640, 1550.

NMR (δ, brom TMS): 2.6–3.6 (5H, m), 4.18 (2H, s), 6.64 (2H, d, J=8 Hz), 6.95 (2H, d, J=8 Hz), 7.19 (5H, s), 9.15 (1H, s), 17.95 (1H, s), (disappeared at D$_2$O).

EXAMPLE 19

Synthesis of 2-(4-chlorophenyl)carbamoyl-5-phenyl-cyclohexane-1,3-dione

In 50 ml of dry dimethylformamide was dissolved 3.76 g of 5-phenyl-cyclohexane-1,3-dione, and 0.3 ml of triethylamine was added to the solution and 3.48 g of 4-chlorophenylisocyanate was added dropwise at room temperature. The mixture was agitated at room temperature for 1 hour, and the mixture was poured into 100 ml of water and the precipitated crystals were recovered by filtration. The crystals were washed with water and recrystallized from 30 ml of ethanol and 20 ml of chloroform to obtain 3.8 g (the yield being 56%) of the desired 2-(4-chlorophenyl)carbamoyl-5-phenyl-cyclohexane-1,3-dione.

Melting Point: 155°–156° C.

Elementary Analysis Values as $C_{19}H_{10}ClNO_3$: Calculated: C=66.77%, H=4.72%, N=4.10%; Found: C=66.60%, H=4.73%, N=4.06%.

IR (cm$^{-1}$, nujol): 1640, 1600, 1550, 813.

NMR (δ, brom TMS): 2.6–3.5 (5H, m), 7.25 (5H, s), 7.09 (2H, d, J=9 Hz), 7.33 (2H, d, J=9 Hz), 11.87 (1H, s) (disappeared at D$_2$O).

EXAMPLES 20 through 98

The compounds shown in Table 4 were prepared according to the process of Example 15 (for Examples 20 through 58), Example 16 (for Examples 59 through 83) or Example 19 (for Example 84 through 98).

TABLE 4

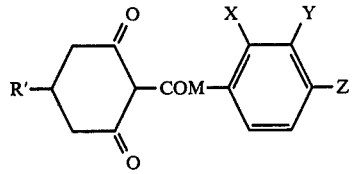

| Example No. | R' | M | X | Y | Z | Melting Point (°C.) | Molecular Formula | Elementary Analysis Values (%) (upper value: calculated value, lower value: found value) C | H |
|---|---|---|---|---|---|---|---|---|---|
| 20 | phenyl- | —(CH$_2$)$_2$— | —H | —H | —H | 98–99 | $C_{21}H_{20}O_3$ | 78.72 / 78.49 | 6.29 / 6.17 |
| 21 | phenyl- | —(CH$_2$)$_2$— | —H | —H | —OCH$_3$ | 122 | $C_{22}H_{22}O_4$ | 75.41 / 75.58 | 6.33 / 6.36 |
| 22 | phenyl- | —(CH$_2$)$_2$— | —H | —H | —Cl | 104.5–106 | $C_{21}H_{19}ClO_3$ | 71.09 / 71.24 | 5.40 / 5.49 |
| 23 | phenyl- | —(CH$_2$)$_2$— | —H | —H | —CH$_3$ | 92.5 | $C_{22}H_{22}O_3$ | 79.01 / 79.01 | 6.63 / 6.64 |
| 24 | phenyl- | —(CH$_2$)$_2$— | —Cl | —H | —H | 100–101 | $C_{21}H_{19}ClO_3$ | 71.09 / 71.39 | 5.40 / 5.58 |
| 25 | phenyl- | —(CH$_2$)$_2$— | —OCH$_3$ | —H | —H | 135–136 | $C_{22}H_{22}O_4$ | 75.41 / 75.34 | 6.33 / 6.44 |

TABLE 4-continued

| Example No. | R' | M | X | Y | Z | Melting Point (°C.) | Molecular Formula | Elementary Analysis Values (%) (upper: calculated, lower: found) | |
|---|---|---|---|---|---|---|---|---|---|
| 26 | phenyl | $-(CH_2)_2-$ | $-Cl$ | $-H$ | $-Cl$ | 99–100 | $C_{21}H_{18}Cl_2O_3$ | 64.79 / 65.16 | 4.66 / 4.78 |
| 27 | phenyl | $-(CH_2)_2-$ | $-OCH_3$ | $-OCH_3$ | $-OCH_3$ | 94–95 | $C_{24}H_{26}O_6$ | 70.23 / 70.16 | 6.39 / 6.34 |
| 28 | phenyl | $-(CH_2)_2-$ | $-H$ | $-H$ | $-SO_2CH_3$ | 176–177 | $C_{22}H_{22}O_5S$ | 66.31 / 66.57 | 5.57 / 5.59 |
| 29 | phenyl | $-(CH_2)_2-$ | $-H$ | $-H$ | $-CN$ | 119 | $C_{22}H_{19}NO_3$ | 76.51 / 76.53 | 5.55 / 5.58 |
| 30 | phenyl | $-(CH_2)_2-$ | $-H$ | $-OCH_3$ | $-OCH_3$ | 101.5 | $C_{23}H_{24}O_5$ | 72.61 / 72.56 | 6.36 / 6.34 |
| 31 | phenyl | $-(CH_2)_2-$ | $-H$ | $-OCH_3$ | $-H$ | 81–82 | $C_{22}H_{22}O_4$ | 75.41 / 75.48 | 6.33 / 6.41 |
| 32 | phenyl | $-(CH_2)_2-$ | $-H$ | $-H$ | $-OH$ | 205–206 | $C_{21}H_{20}O_4$ | 74.98 / 74.76 | 5.99 / 6.02 |
| 33 | phenyl | $-(CH_2)_2-$ | $-H$ | $-OH$ | $-H$ | 159–160 | $C_{21}H_{20}O_4$ | 74.98 / 74.91 | 5.99 / 6.03 |
| 34 | phenyl | $-(CH_2)_2-$ | $-H$ | $-OH$ | $-OCH_3$ | 156 | $C_{22}H_{22}O_5$ | 72.09 / 72.16 | 6.07 / 6.10 |
| 35 | phenyl | $-(CH_2)_2-$ | $-H$ | $-OCOCH_3$ | $-OCOCH_3$ | 102 | $C_{25}H_{24}O_7$ | 68.80 / 68.94 | 5.54 / 5.67 |
| 36 | phenyl | $-(CH_2)_2-$ | $-H$ | $-H$ | $-H$ | 110–111 | $C_{21}H_{19}FO_3$ | 74.54 / 75.06 | 5.56 / 5.79 |
| 37 | phenyl | $-(CH_2)_2-$ | $-H$ | $-H$ | $-OC_2H_5$ | 101.5 | $C_{23}H_{24}O_4$ | 75.80 / 76.01 | 6.64 / 6.65 |
| 38 | phenyl | $-(CH_2)_2-$ | $-H$ | $-H$ | $-OC_3H_7$ | 99.5–100 | $C_{24}H_{26}O_4$ | 76.16 / 76.10 | 6.93 / 6.83 |
| 39 | $CH_3O-$phenyl | $-(CH_2)_2-$ | $-H$ | $-H$ | $-OCH_3$ | 100.5 | $C_{23}H_{24}O_5$ | 72.61 / 72.31 | 6.36 / 6.36 |
| 40 | $CH_3O-$phenyl | $-(CH_2)_2-$ | $-H$ | $-H$ | $-Cl$ | 97 | $C_{22}H_{21}ClO_4$ | 68.73 / 68.64 | 5.51 / 5.56 |
| 41 | $CH_3O-$phenyl | $-(CH_2)_2-$ | $-Cl$ | $-H$ | $-H$ | 93 | $C_{22}H_{21}ClO_4$ | 68.73 / 68.91 | 5.51 / 5.59 |
| 42 | $CH_3O-$phenyl | $-(CH_2)_2-$ | $-H$ | $-OH$ | $-OH$ | 195–196 | $C_{22}H_{22}O_6$ | 69.10 / 68.91 | 5.80 / 5.60 |

TABLE 4-continued

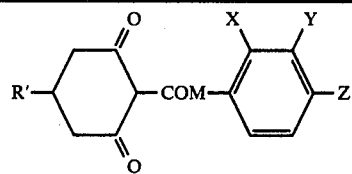

| Example No. | R' | M | X | Y | Z | Melting Point (°C.) | Molecular Formula | Elementary Analysis Values (%) (upper value: calculated value, lower value: found value) | |
|---|---|---|---|---|---|---|---|---|---|
| 43 | CH$_3$O—⟨phenyl⟩— | —(CH$_2$)$_2$— | —H | —H | —H | 112.5 | C$_{22}$H$_{22}$O$_4$ | 75.41<br>75.32 | 6.33<br>6.04 |
| 44 | ⟨phenyl-OCH$_3$⟩— | —(CH$_2$)$_2$— | —H | —OH | —OH | 209–210 | C$_{22}$H$_{22}$O$_6$ | 69.10<br>69.03 | 5.80<br>5.95 |
| 45 | ⟨phenyl-OCH$_3$⟩— | —(CH$_2$)$_2$— | —H | —H | —H | 75 | C$_{22}$H$_{22}$O$_4$ | 75.41<br>75.61 | 6.33<br>6.23 |
| 46 | Cl—⟨phenyl⟩— | —(CH$_2$)$_2$— | —Cl | —H | —H | 97–98 | C$_{21}$H$_{18}$Cl$_2$O$_3$ | 64.79<br>65.58 | 4.66<br>4.77 |
| 47 | Cl—⟨phenyl⟩— | —(CH$_2$)$_2$— | —OCH$_3$ | —OCH$_3$ | —OCH$_3$ | 108.5 | C$_{24}$H$_{25}$ClO$_6$ | 64.79<br>64.89 | 5.66<br>5.70 |
| 48 | CH$_3$—⟨phenyl⟩— | —(CH$_2$)$_2$— | —H | —OH | —OH | 233–235 | C$_{22}$H$_{22}$O$_5$ | 72.51<br>72.08 | 5.53<br>5.94 |
| 49 | CH$_3$—⟨phenyl⟩— | —(CH$_2$)$_2$— | —H | —H | —H | 106.5–107 | C$_{22}$H$_{22}$O$_3$ | 79.01<br>79.45 | 6.63<br>6.71 |
| 50 | CH$_3$—⟨phenyl⟩— | —(CH$_2$)$_2$— | —Cl | —H | —H | 115.5–117 | C$_{22}$H$_{21}$ClO$_3$ | 71.64<br>71.71 | 5.74<br>5.84 |
| 51 | ⟨methylenedioxyphenyl⟩— | —(CH$_2$)$_2$— | —H | —H | —H | 88 | C$_{22}$H$_{20}$O$_5$ | 72.51<br>72.28 | 5.53<br>5.60 |
| 52 | ⟨methylenedioxyphenyl⟩— | —(CH$_2$)$_2$— | —H | —OH | —OH | 223–224 | C$_{22}$H$_{20}$O$_7$ | 66.66<br>66.67 | 5.09<br>5.12 |
| 53 | OH—⟨phenyl⟩— | —(CH$_2$)$_2$— | —H | —H | —H | 124 | C$_{21}$H$_{20}$O$_4$ | 74.98<br>75.26 | 5.99<br>5.86 |
| 54 | OH—⟨phenyl⟩— | —(CH$_2$)$_2$— | —H | —OH | —OH | 223.5–225 | C$_{21}$H$_{20}$O$_6$ | 68.47<br>68.65 | 5.47<br>5.43 |
| 55 | HO—⟨phenyl⟩— | —(CH$_2$)$_2$— | —H | —H | —H | 145–146 | C$_{21}$H$_{20}$O$_4$ | 74.98<br>75.11 | 5.99<br>5.75 |
| 56 | HO—⟨phenyl⟩— | —(CH$_2$)$_2$— | —H | —OH | —OH | 246–247 | C$_{21}$H$_{20}$O$_6$ | 68.47<br>68.28 | 5.47<br>5.45 |

TABLE 4-continued

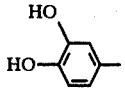

| Example No. | R' | M | X | Y | Z | Melting Point (°C.) | Molecular Formula | Elementary Analysis Values (%) (upper value: calculated value, lower value: found value) | |
|---|---|---|---|---|---|---|---|---|---|
| 57 | HO-, HO- (dihydroxyphenyl) | —(CH$_2$)$_2$— | —H | —H | —H | 177–178 | C$_{21}$H$_{20}$O$_5$ | 71.58 / 71.85 | 5.72 / 5.81 |
| 58 | HO-, HO- (dihydroxyphenyl) | —(CH$_2$)$_2$— | —H | —OH | —OH | 224–225 | C$_{21}$H$_{20}$O$_7$ | 65.61 / 65.66 | 5.24 / 5.07 |
| 59 | phenyl | —CH$_2$— | —H | —H | —Cl | 110–112 | C$_{20}$H$_{17}$ClO$_3$ | 70.48 / 70.38 | 5.03 / 5.03 |
| 60 | phenyl | —CH$_2$— | —Cl | —H | —H | 85–86 | C$_{20}$H$_{17}$ClO$_3$ | 70.48 / 70.36 | 5.03 / 5.04 |
| 61 | phenyl | —CH$_2$— | —Cl | —H | —Cl | 110 | C$_{20}$H$_{16}$Cl$_2$O$_3$ | 64.01 / 63.85 | 4.30 / 4.27 |
| 62 | phenyl | —CH$_2$— | —H | —H | —OCH$_3$ | 98 | C$_{21}$H$_{20}$O$_4$ | 74.98 / 75.27 | 5.99 / 6.01 |
| 63 | phenyl | —CH$_2$— | —H | —H | —CH$_3$ | 97–98 | C$_{21}$H$_{20}$O$_3$ | 78.72 / 79.04 | 6.29 / 6.43 |
| 64 | phenyl | —CH$_2$— | —NO$_2$ | —H | —H | 118.5–119 | C$_{20}$H$_{17}$NO$_5$ | 68.37 / 68.30 | 4.88 / 4.88 |
| 65 | phenyl | —CH$_2$— | —OCH$_3$ | —H | —H | 142–143 | C$_{21}$H$_{20}$O$_4$ | 74.98 / 75.05 | 5.99 / 5.95 |
| 66 | phenyl | —CH$_2$— | —OCH$_2$-phenyl | —H | —H | 143–144 | C$_{27}$H$_{24}$O$_4$ | 78.62 / 79.00 | 5.86 / 5.94 |
| 67 | phenyl | —CH$_2$— | —OH | —H | —H | 153 | C$_{20}$H$_{16}$O$_4$ | 74.52 / 74.19 | 5.63 / 5.77 |
| 68 | phenyl | —CH$_2$— | —OCH$_3$ | —OCH$_3$ | —OCH$_3$ | 95.5 | C$_{20}$H$_{24}$O$_6$ | 69.68 / 69.59 | 6.10 / 6.16 |
| 69 | phenyl | —CH$_2$— | —OCH$_2$-phenyl | —OCH$_3$ | —H | 110 | C$_{28}$H$_{26}$O$_5$ | 76.00 / 75.84 | 5.92 / 5.98 |
| 70 | phenyl | —CH$_2$— | —OH | —OCH$_3$ | —H | 159–160 | C$_{21}$H$_{20}$O$_5$ | 71.58 / 71.30 | 5.72 / 5.78 |
| 71 | Cl-phenyl | —CH$_2$— | —H | —H | —H | 120–121 | C$_{20}$H$_{17}$ClO$_3$ | 70.49 / 70.43 | 5.02 / 5.23 |
| 72 | Cl-phenyl | —CH$_2$— | —Cl | —H | —Cl | 142–143 | C$_{20}$H$_{15}$Cl$_3$O$_3$ | 58.63 / 58.37 | 3.69 / 3.73 |

TABLE 4-continued

Structure:
R'—[cyclohexane-1,3-dione with 2-COM-aryl substituent]—aryl(X,Y,Z)

| Example No. | R' | M | X | Y | Z | Melting Point (°C.) | Molecular Formula | Elementary Analysis Values (%) (upper: calculated, lower: found) | |
|---|---|---|---|---|---|---|---|---|---|
| 73 | 4-Cl-C$_6$H$_4$- | —CH$_2$— | —H | —H | —OCH$_3$ | 127 | C$_{21}$H$_{19}$ClO$_4$ | 68.00 / 67.83 | 5.16 / 5.00 |
| 74 | 4-Cl-C$_6$H$_4$- | —CH$_2$— | —H | —H | —CH$_3$ | 129–130 | C$_{21}$H$_{19}$ClO$_3$ | 71.07 / 71.10 | 5.40 / 5.36 |
| 75 | 4-Cl-C$_6$H$_4$- | —CH$_2$— | —Cl | —H | —H | 129–129.5 | C$_{20}$H$_{16}$ClO$_3$ | 64.01 / 64.00 | 4.30 / 4.23 |
| 76 | 2-furyl | —CH$_2$— | —Cl | —H | —Cl | 123 | C$_{18}$H$_{14}$Cl$_2$O$_4$ | 59.19 / 59.04 | 3.86 / 3.91 |
| 77 | 2-furyl | —CH$_2$— | —H | —H | —Cl | 109–110 | C$_{18}$H$_{15}$ClO$_4$ | 65.35 / 65.67 | 4.57 / 4.47 |
| 78 | 2-furyl | —CH$_2$— | —Cl | —H | —H | 82–83 | C$_{18}$H$_{15}$ClO$_4$ | 65.35 / 65.28 | 4.57 / 4.51 |
| 79 | 2-furyl | —CH$_2$— | —H | —H | —OCH$_3$ | 108 | C$_{19}$H$_{18}$O$_5$ | 69.93 / 68.81 | 5.56 / 5.45 |
| 80 | 2-furyl | —CH$_2$— | —H | —H | —CH$_3$ | 89–90 | C$_{19}$H$_{18}$O$_4$ | 73.53 / 73.37 | 5.85 / 5.89 |
| 81 | 2-furyl | —CH$_2$— | —NO$_2$ | —H | —H | 133–133.5 | C$_{18}$H$_{15}$NO$_6$ | 63.34 / 63.40 | 4.43 / 4.34 |
| 82 | C$_6$H$_5$- | — | —H | —H | —H | 142–142.5 | C$_{19}$H$_{16}$O$_3$ | 78.06 / 78.14 | 5.52 / 5.38 |
| 83 | C$_6$H$_5$- | — | —H | —H | —Cl | 156 | C$_{19}$H$_{15}$ClO$_3$ | 69.82 / 70.08 | 4.63 / 4.49 |

| Example No. | R' | M | X | Y | Z | Melting Point (°C.) | Molecular Formula | C | H | N |
|---|---|---|---|---|---|---|---|---|---|---|
| 84 | C$_6$H$_5$- | —NH— | —Cl | —H | —H | 142–143 | C$_{19}$H$_{16}$ClNO$_3$ | 66.77 / 66.34 | 4.72 / 4.69 | 4.10 / 4.26 |
| 85 | C$_6$H$_5$- | —NH— | —F | —H | —H | 127.5–128 | C$_{19}$H$_{16}$FNO$_3$ | 70.14 / 70.00 | 4.96 / 5.03 | 4.31 / 4.40 |
| 86 | C$_6$H$_5$- | —NH— | —H | —H | —F | 160 | C$_{19}$H$_{16}$FNO$_3$ | 70.14 / 69.71 | 4.96 / 4.77 | 4.31 / 4.18 |
| 87 | 4-Cl-C$_6$H$_4$- | —NH— | —H | —H | —Cl | 151–151.5 | C$_{19}$H$_{15}$Cl$_2$NO$_3$ | 60.66 / 60.35 | 4.02 / 4.00 | 3.72 / 3.75 |
| 88 | 4-Cl-C$_6$H$_4$- | —NH— | —Cl | —H | —H | 173–175 | C$_{19}$H$_{15}$Cl$_2$NO$_3$ | 60.66 / 60.59 | 4.02 / 4.00 | 3.72 / 3.82 |

TABLE 4-continued $$R'-\underset{O}{\overset{O}{\bigcirc}}-COM-\underset{Z}{\overset{X\ Y}{\bigcirc}}$$

| Example No. | R' | M | X | Y | Z | Melting Point (°C.) | Molecular Formula | Elementary Analysis Values (%) (upper value: calculated value, lower value: found value) | | |
|---|---|---|---|---|---|---|---|---|---|---|
| 89 | Cl—⟨⟩— | —NH— | —H | —H | —F | 159 | C₁₉H₁₅ClFNO₃ | 63.42 | 4.20 | 3.89 |
| | | | | | | | | 63.49 | 4.32 | 3.84 |
| 90 | ⟨O⟩— | —NH— | —H | —H | —Cl | 160.5 | C₁₇H₁₄ClNO₄ | 61.55 | 4.25 | 4.22 |
| | | | | | | | | 61.60 | 4.25 | 4.35 |
| 91 | ⟨O⟩— | —NH— | —Cl | —H | —H | 123 | C₁₇H₁₄ClNO₄ | 61.55 | 4.25 | 4.22 |
| | | | | | | | | 61.53 | 4.23 | 4.29 |
| 92 | ⟨O⟩— | —NH— | —F | —H | —H | 140–141 | C₁₇H₁₄FNO₄ | 64.76 | 4.48 | 4.44 |
| | | | | | | | | 64.53 | 4.47 | 4.35 |
| 93 | ⟨O⟩— | —NH— | —H | —H | —F | 141 | C₁₇H₁₄FNO₄ | 64.76 | 4.48 | 4.44 |
| | | | | | | | | 64.53 | 4.45 | 4.51 |

When the compounds of formula [I], according to the present invention, and salts thereof, are used as antihypertensive agents for treatment of various hypertensions such as essential hypertension, renal hypertension and malignant hypertension, they are administered orally or non-orally (intermuscular, hypodermic or intravenous administration or in the form of suppositories). The administration doses are changed appropriately according to the body weight and age of the patient, the disease condition, the application method and other factors, but generally, they are administered to adult humans in amounts of 10 to 1,500 mg per day.

The compounds of the present invention are formed into tablets, granules, powders, capsules, injectable solutions, suppositories and the like according to processes customarily employed in the art.

When a solid medicine for oral administration is prepared, an excipient is added to the active ingredient, and adjuvants such as a binder, a disintegrator, a lubricant, a colorant, an odor improver and a taste improver are added. Then, the mixture is formed into tablets, coated tablets, granules, powders and capsules according to customary procedures.

As the excipient, there are used, for example, lactose, corn starch, white sugar, glucose, sorbitol and crystalline cellulose, and as the binder, there are used, for example, polyvinyl alcohol, polyvinyl ether, ethyl cellulose, methyl cellulose, gum arabic, tragacanth gum, gelatin, shellac, hydroxyethyl cellulose, hydroxypropyl cellulose, polyvinyl pyrrolidone, white sugar and sorbitol. As the disintegrator, there are used, for example, starch, agar, powdery gelatin, crystalline cellulose, calcium carbonate, sodium hydrogencarbonate, calcium citrate, dextrin, pectin and calcium carboxymethyl cellulose, and as the lubricant, there are used, for example, magnesium stearate, talc, polyethylene glycol, silica and hardened vegetable oils. Colorants which are officially allowed to be incorporated into medicines are used, and as the odor or taste improver, there are used, for example, cacao powder, menthol, aromatic powder, peppermint oil and cinnamon powder. Tablets and granules may be coated with sugar, gelatin or the like.

When a liquid preparation for oral administration is formed, appropriate adjuvants such as an odor or taste improver, a buffering agent and a stabilizer are added to the active ingredient according to need and the mixture is formed into a syrup according to customary procedures.

When an injectable solution is formed, appropriate adjuvants such as a pH-adjusting agent, a buffering agent, a suspending agent, a solubilizing assistant, a stabilizer, an isotonic agent and a preserving agent are added to the active ingredient according to need, and the mixture is formed into hypodermic, intramuscular and intravenous injections according to customary procedures.

As the suspending agent, there are used, for example, methyl cellulose, Polysorbate 80, hydroxyethyl cellulose, gum arabic, tragacanth powder, sodium carboxymethyl cellulose and polyoxyethylene sorbitan monolaurate, and as the solubilizing assistant, there are used, for example, polyoxyethylene-hardened castor oil, Polysorbate 80, nicotinic amide, polyoxyethylene sorbitan monolaurate, macrogol, and castor oil fatty acid ether ester. As the stabilizing agent, there are used, for example, sodium sulfite, sodium metasulfite and diethyl ether, and as the preserving agent, there are used, for example, methyl p-hydroxybenzoate, ethyl p-hydroxybenzoate, sorbic acid, phenol, cresol and chlorocresol.

The present invention will now be described more specifically with reference to the following illustrative Examples of medicinal preparations. Of course, these Examples by no means limit the scope of the invention.

| Medicinal Preparation Example 1 (Tablet) | |
|---|---|
| 5-Phenyl-2-[3-(2,2-dimethyl-1,3-benzo-dioxol-5-yl)-propionyl]-cyclohexane-1,3-dione | 100 g |
| Corn starch | 10 g |
| Lactose | 20 g |
| Calcium carboxymethyl cellulose | 15 g |
| Microcrystalline cellulose | 40 g |
| Polyvinyl pyrrolidone | 5 g |
| Talc | 10 g |

Tablets having a weight of 200 mg were prepared according to the above recipe by a customary tablet-forming method.

| Medicinal Preparation Example 3 (Capsule) | |
|---|---|
| 5-(1-Methoxyphenyl)-2-[3-(3,4-methylene-dioxyphenyl)-propionyl]-cyclohexane-1,3-dione | 100 g |
| Lactose | 100 g |

According to the above recipe, capsules were prepared by a customary method so that 200 mg of the above composition was packed into one capsule.

| Medicinal Preparation Example 3 (Tablet) | |
|---|---|
| 5-Phenyl-2-phenylacetyl-cyclohexane-1,3-dione | 100 g |
| Corn starch | 10 g |
| Lactose | 20 g |
| Calcium carboxymethyl cellulose | 15 g |
| Microcrystalline cellulose | 40 g |
| Polyvinyl pyrrolidone | 5 g |
| Talc | 10 g |

Tablets having a weight of 200 mg were prepared according to the above recipe by a customary tablet-forming method.

| Medicinal Preparation Example 4 (Capsule) | |
|---|---|
| 2-(4-Chlorophenyl)carbamoyl-5-phenyl-cyclohexane-1,3-dione | 100 g |
| Lactose | 100 g |

According to the above recipe, capsules were prepared by a customary method so that 200 mg of the above composition was packed into one capsule.

The embodiments of the invention in which an exclusive property or privilege is claimed are defined as follows:

1. A compound having the formula

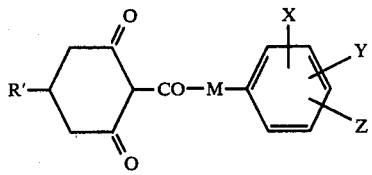

in which
(1) R' is phenyl, furyl or substituted phenyl, in which said substituted phenyl is substituted with from 1 to 5 substituents which are the same or different and are selected from the group consisting of alkyl having 1 to 6 carbon atoms, alkoxy having 1 to 6 carbon atoms, hydroxy, halogen, halogenated alkyl having 1 to 6 carbon atoms, amino, mono- or di-alkyl amino in which the alkyl has 1 to 6 carbon atoms and —O—(CH$_2$)$_a$—O— bonded to any two adjacent carbon atoms of the phenyl nucleus and in which "a" is 1 or 2;

(2) M is —(CH$_2$)—$_m$, wherein "m" is zero or an integer from 1 to 4;

(3) X, Y and Z, which can be the same or different, are hydrogen, lower alkyl, lower alkoxy, lower alkyl carbonyloxy, hydroxy, lower alkyl sulfonyl, nitro, cyano or halogen; and pharmacologically acceptable salts thereof.

2. A compound according to claim 1 having the formula:

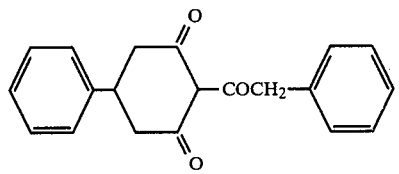

and pharmacologically acceptable salts thereof.

3. A compound according to claim 1 having the formula:

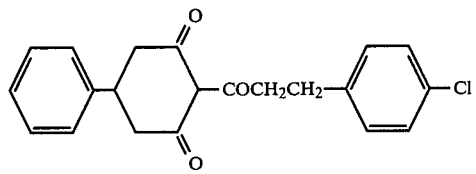

and pharmacologically acceptable salts thereof.

4. A compound according to claim 1 having the formula:

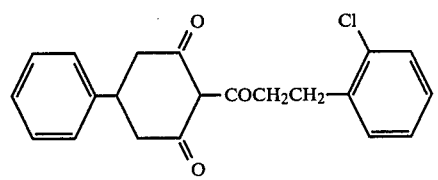

and pharmacologically acceptable salts thereof.

5. A compound according to claim 1 having the formula:

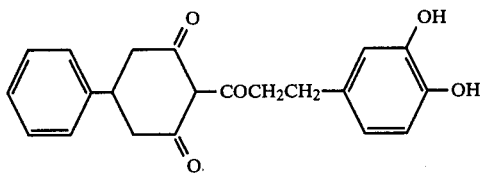

and pharmacologically acceptable salts thereof.

6. A compound according to claim 1 having the formula:

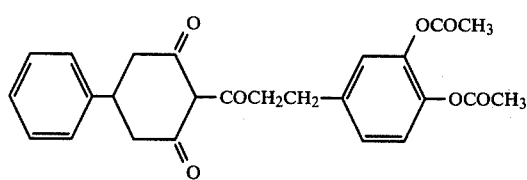

and pharmacologically acceptable salts thereof.

7. A compound according to claim 1 having the formula:

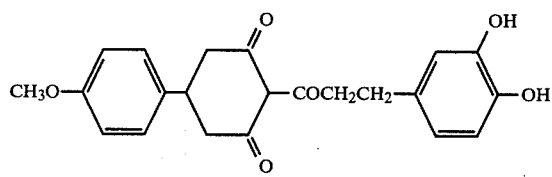

and pharmacologically acceptable salts thereof.

8. A compound according to claim 1 having the formula:

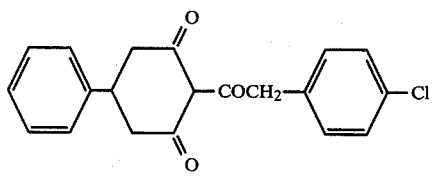

and pharmacologically acceptable salts thereof.

9. A compound according to claim 1 having the formula:

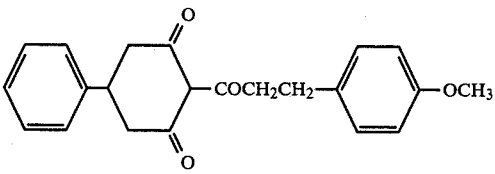

and pharmacologically acceptable salts thereof.

10. A composition for treating hypertension comprising an effective amount of a compound as defined in claim 1 mixed with a pharmaceutical carrier.

11. A method treating a subject suffering from hypertension which comprises administering to that subject an effective antihypertensive amount of a compound having the formula

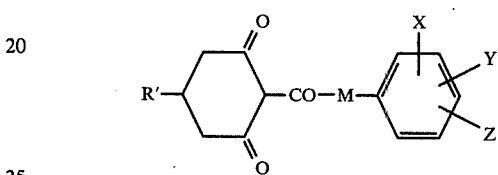

in which
(1) R' is phenyl, furyl or substituted phenyl, in which said substituted phenyl is substituted with from 1 to 5 substituents which are the same or different and are selected from the group consisting of alkyl having 1 to 6 carbon atoms, alkoxy having 1 to 6 carbon atoms, hydroxy, halogen, halogenated alkyl having 1 to 6 carbon atoms, amino, mono-or dialkyl amino in which the alkyl has 1 to 6 carbon atoms and —O—$(CH_2)_a$—O— bonded to any two adjacent carbon atoms of the phenyl nucleus and in which "a" is 1 or 2;
(2) M is —$(CH_2)_m$— or —NH—, wherein "m" is zero or an integer from 1 to 4;
(3) X, Y and Z, which can be the same or different, are hydrogen, lower alkyl, lower alkoxy, lower alkyl carbonyloxy, hydroxy, lower alkyl sulfonyl, nitro, cyano or halogen;
and pharmacologically acceptable salts thereof.

* * * * *